(12) United States Patent
Edwards

(10) Patent No.: US 6,425,877 B1
(45) Date of Patent: Jul. 30, 2002

(54) TREATMENT OF TISSUE IN THE DIGESTIVE CIRCULATORY RESPIRATORY URINARY AND REPRODUCTIVE SYSTEMS

(75) Inventor: Stuart D. Edwards, Portola Valley, CA (US)

(73) Assignee: Novasys Medical, Inc., Newark, CA (US)

(*) Notice: Subject to any disclaimer, the term of this patent is extended or adjusted under 35 U.S.C. 154(b) by 0 days.

(21) Appl. No.: 09/307,348

(22) Filed: May 6, 1999

Related U.S. Application Data

(63) Continuation-in-part of application No. 09/285,575, filed on Apr. 2, 1999.

(51) Int. Cl.⁷ .................. A61N 1/30; A61N 1/00; A61M 29/00; A61B 18/18
(52) U.S. Cl. .............. 604/21; 604/101.05; 604/103.01; 606/41; 606/192; 607/116
(58) Field of Search ................. 604/20, 21, 96.01, 604/102.01, 101.02, 103.01, 103.02, 103.03, 101.03, 101.05, 102.02; 606/27, 32, 33, 41, 46–50, 191–194; 607/100–105, 116, 138

(56) References Cited

U.S. PATENT DOCUMENTS

| | | | | |
|---|---|---|---|---|
| 5,374,261 A | * | 12/1994 | Yoon | 604/385.1 |
| 5,425,703 A | * | 6/1995 | Feiring | 604/21 |
| 5,443,470 A | * | 8/1995 | Stern et al. | 607/98 |
| 5,505,730 A | * | 4/1996 | Edwards | 606/41 |
| 5,704,908 A | * | 1/1998 | Hofmann et al. | 604/21 |
| 5,769,880 A | * | 6/1998 | Truckai et al. | 607/101 |
| 6,254,599 B1 | * | 7/2001 | Lesh et al. | 606/41 |

* cited by examiner

Primary Examiner—Michael J. Hayes
(74) Attorney, Agent, or Firm—Michael A. Glenn; Christopher Peil

(57) ABSTRACT

Apparatus for creating a controlled pattern of ablation throughout the interior of an organ or body cavity while minimizing thermal damage to collateral tissue includes a microporous balloon mounted on a catheter. The balloon, bearing electrodes embedded in the surface, is inserted into the target body region and inflated, whereupon the electrodes come into contact with the interior of the targeted organ. Because of its microporous nature, fluids for cooling or various therapeutic purposes may pass through the surface of the balloon to the target site. Sensors monitor conditions such as temperature and impedance at the site, providing required feedback for delivery of RF energy for ablation, and administration of cooling and hydrating fluids. A second balloon or other means isolates the treatment area and controls the flow and accumulation of body fluids and treatment fluids minimizing adverse treatment effects from fluid accumulations, and anchoring the catheter in place.

15 Claims, 18 Drawing Sheets

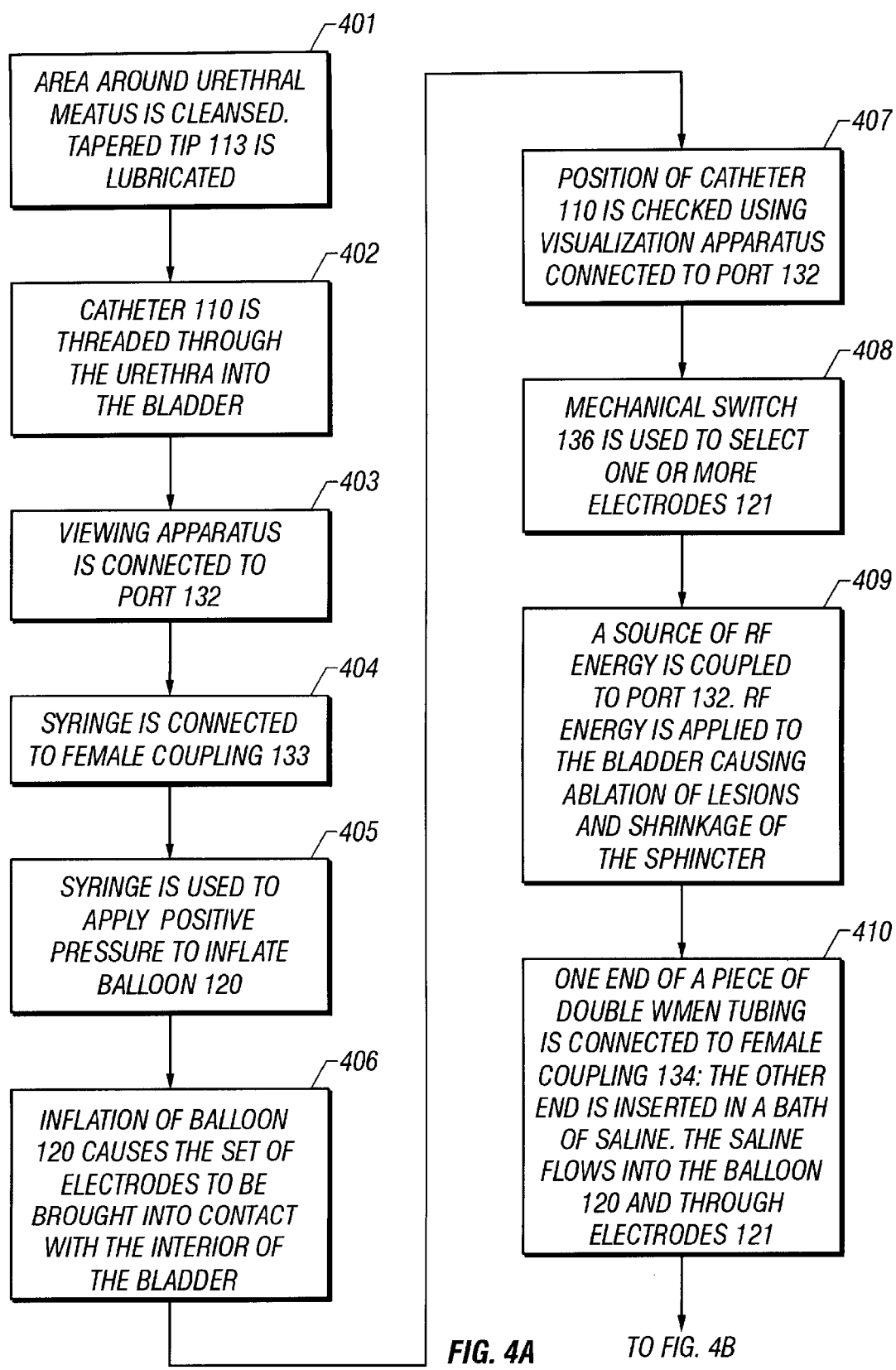

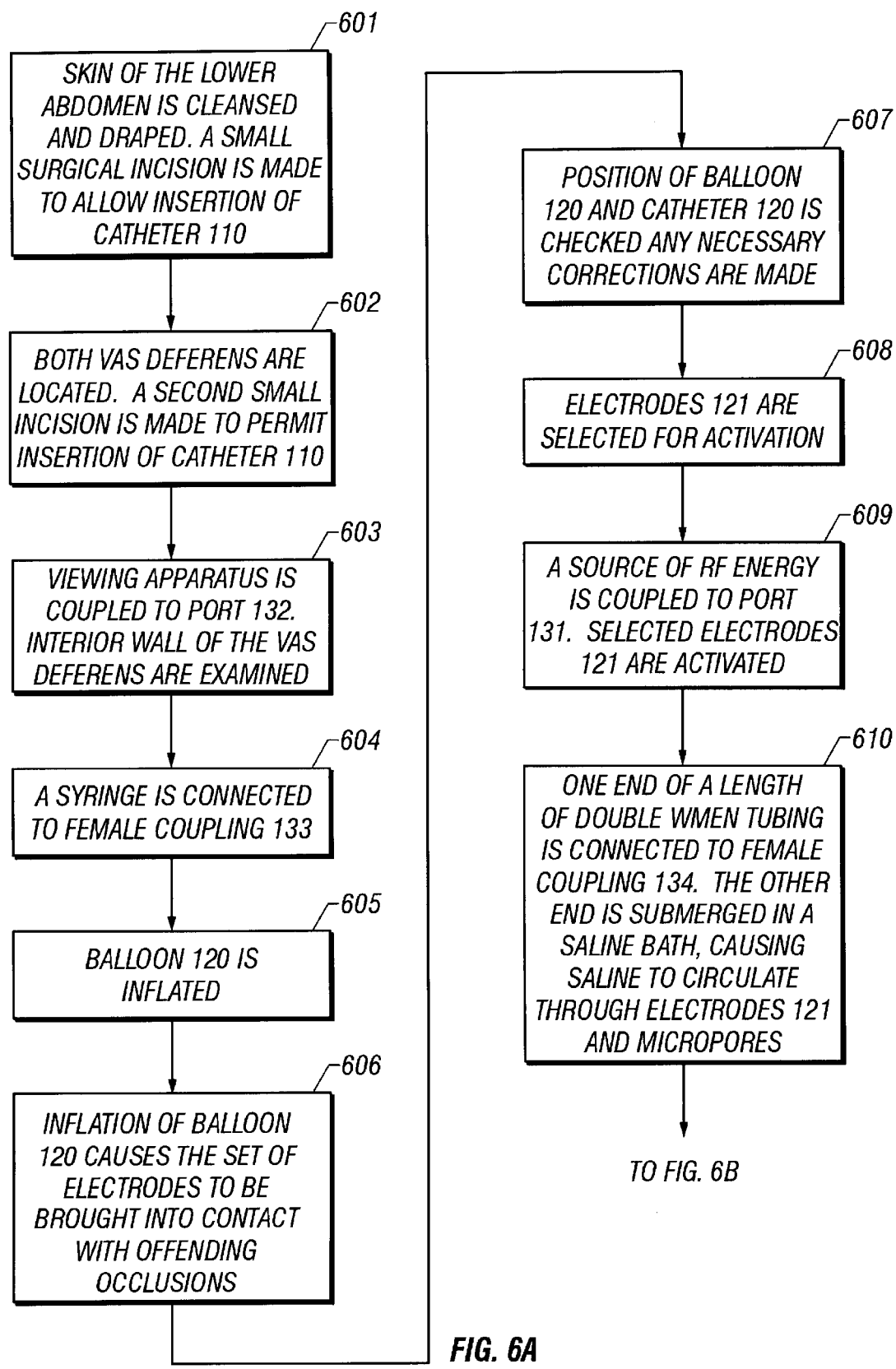

TREATMENT OF TISSUE IN THE DIGESTIVE CIRCULATORY RESPIRATORY URINARY AND REPRODUCTIVE SYSTEMS

CROSS REFERENCE TO RELATED APPLICATION

This Application is a Continuation-in-part of U.S. patent application Ser. No. 09/285,575, filed on Apr. 2, 1999; entitled "Treating Body Tissue by Applying Energy and Substances."

BACKGROUND OF THE INVENTION

1. Field of the Invention

This invention relates to treatment of tissue, particularly in the sphincters and other muscles of the digestive, circulatory, respiratory, urinary and reproductive systems. Such treatment can be performed using ablation, coating, expansion, plumping, shaping, shrinking, or related techniques.

2. Related Art

The circulatory, respiratory, urinary, reproductive and digestive systems of human beings, livestock and other mammals are subject to a number of disorders and diseases. Disorders in the circulatory system include aneurysms of the aortic arch, thoracic aorta and abdominal aorta. Disorders in the respiratory system include occlusion of the trachea and tumors and polyps in the hypopharynx, oropharynx, nasopharnyx and larynx. Disorders in the urinary system include incontinence and urinary neuropathy. Disorders of the reproductive system include obstruction of the vas deferens, obstruction of the fallopian tubes, uterine cysts and fibroids, prolapsed uterus, menorrhagia and tumors or cancerous tissue. Disorders in the digestive system include Barrett's esophagus, occlusion of the bile ducts, occlusion of the pancreatic ducts, tumors and cancerous tissue found in the stomach and related structures. Other disorders in the rectum and colon include hemorrhoids (external and internal), fecal incontinence, prolapsed rectal muscles, rectal muscle spasms, anal fissures, polyps, diverticulosus, diverticulitus and pilonital cysts.

Known methods for the treatment of these disorders include surgery, pharmaceutical remedies, chemotherapeutic regimens, radiation, photodynamic therapy and lifestyle modification. These methods only occasionally achieve the goal of successful treatment of known disorders. One problem in the known art is that these methods suffer from several drawbacks.

Drawbacks to surgical treatment include its highly invasive nature, associated risks, possible iatrogenic effects, and high cost. Drawbacks to pharmaceutical and chemotherapeutic treatments include their relative ineffectiveness (particularly in the oral cavity and adjacent respiratory structures) and associated side effects. Moreover, these approaches are contraindicated for many patients. Drawbacks to lifestyle modification include relatively poor patient compliance and relative ineffectiveness. Drawbacks to photodynamic therapy include its frequent unavailability and limited applicability. Drawbacks to radiation include side effects such as exhaustion, radiation burns, chronic dry mouth and permanent distortion of the taste buds. Accordingly, it would be advantageous to provide techniques for treatment of these disorders that are not subject to these known drawbacks.

The use of radio frequency (RF) to ablate tissue in the body (such as heart muscle tissue) is known in the art of cardiac treatment. However, known systems using RF energy are still subject to several drawbacks. One known problem in the art involves the creating a controlled pattern of ablation throughout the interior of an organ. For instance, it is sometimes desirable to apply RF energy to the entire interior of a body cavity such as a urinary bladder. While known systems allow RF energy to be applied to one part of a body cavity, followed by another part, they do not permit the RF energy to be simultaneously directed to the entire interior of a body organ.

A second problem in the known art of applying RF energy involves minimizing thermal damage to adjacent body tissues. Frequently, application of RF energy to targeted tissue results in collateral thermal damage to adjacent tissue because it is difficult to control the temperature of the adjacent structure.

A third problem in the known art is that it can be difficult to block the flow of bodily fluids and gases into an area of the body where tissue ablation is taking place. Bodily fluids can dissipate and detrimentally absorb the energy to be applied to the tissue to be ablated. Dissipation of bodily fluids detracts from the goal of successful tissue ablation and etching.

A fourth problem in the known art involves directing and positioning the electrodes in the body cavity or orifice. Difficulties in accurately positioning the electrodes in the target orifice detract from treatment. Frequently, unhealthy tissue can remain unablated while healthy tissue is removed. Difficulties in directing and positioning the electrodes are particularly problematic because one of the goals of treatment is to minimize collateral damage to healthy tissue and to completely ablate diseased tissue.

A fifth problem in the known art involves difficulty in the simultaneous use of complimentary technology. Known systems do not provide for optimal, simultaneous use of auxiliary tools for visualization, feedback technology and drug administration.

Accordingly, it would be advantageous to provide improved techniques for treatment of disorders in the bladder, esophagus, uterus, fallopian tubes and vas deferens, sinus cavities, aorta, larynx, pharynx and the sphincters and muscle tissue associated with these organs in humans, livestock and other mammals. For example, it would be advantageous to provide devices bearing different arrays of electrodes embedded in an inflatable microporous balloon. Such devices can be coupled to apparatus for drug administration and tissue visualization and mounted on a catheter that can be either manually or laproscopically inserted into a body orifice or organ. Such devices would allow medical or veterinary personnel to (1) provide for the controlled, such as uniform, application of energy throughout the interior of a body cavity, (2) visualize the tissue to be ablated or etched, (2) monitor and regulate the temperature of adjacent tissue, (3) seal off the area from fluids and gases that would disturb the area to be ablated, (4) ablate or otherwise treat diseased tissue while sparing healthy tissue and (5) provide for the localized administration of drugs to numb the area and treat the disorder. These advantages are achieved in an embodiment of the invention in which medical or veterinary personnel use a catheter that supports a multiple array of regularly spaced electrodes embedded in a balloon-like microporous sacs that can be inflated with saline or air. Temperature regulation is achieved by partially infusing the balloon with a circulating fluid whose temperature can be maintained so as to cool the surface of the balloon. Multiple controls for operation of individual electrodes, visualization and drug administration are mounted into the catheter, along with sensors that measure temperature, impedance and other properties.

SUMMARY OF THE INVENTION

The invention provides a method and system for treatment of body structures or tissue. The particular treatment can include one or more of, or some combination of ablation, coating, expansion, plumping, shaping, shrinking, or related techniques. The particular body structures or tissue can include one or more of, or some combination of regions, including the rectum, colon, esophagus, vagina, penis, larynx, pharynx, vas deferens, uterus, trachea, large intestine, small intestine, sinus, bladder, auditory canal, aortic arch, abdominal aorta, thoracic aorta and all associated sphincters as well as smooth and striated muscles.

In a first aspect of the invention, positive pressure is used to inflate a balloon having a microporous membrane with a flowable substance, such as air or saline. Inflation of the balloon inside a targeted organ causes a set of electrodes, either embedded in or otherwise positioned with regard to, the microporous balloon to come into contact with either a portion of, or the entire interior of, the targeted organ. Negative pressure can deflate the balloon and allow the catheter to be removed from the body without damaging adjacent body structures.

In a second aspect of the invention, the electrodes are coupled to sensors that measure sympathetic and parasympathetic nervous activity in selected areas of the targeted region. These measurements are useful both in making diagnostic assessments as well as in determining treatment parameters.

In a third aspect of the invention, the electrodes are coupled to sensors that measure properties of the target region such as temperature and impedance. Measurement of these properties permits the use of feedback technique to control delivery of the RF energy and administration of fluids for cooling and hydrating the affected tissues.

In a fourth aspect of the invention, an environment proximate to or surrounding the targeted treatment region can be isolated or controlled by blocking the flow of gases or liquids using an inflatable balloon or other device positioned proximate to the tissue that is to be ablated. The inflatable balloon can also serve to anchor the catheter in place and prevent the catheter from being expelled from the body. The inflatable balloon can also insure that locally administered drugs remain in the area where most effective or needed.

In a fifth aspect of the invention, the catheter includes an optical path that can be coupled to external viewing apparatus. The position of the electrodes in the body can therefore be determined by fluoroscopic, fiber optic, or radioscopic techniques.

BRIEF DESCRIPTION OF THE DRAWINGS

FIGS. 4A and 4B is a process flow diagram of a method for treatment of incontinence in men.

FIGS. 6A and 6B is a process flow diagram of a method for treatment of an occluded vas deferens.

DETAILED DESCRIPTION OF THE PREFERRED EMBODIMENT

System Elements

Figure 1:
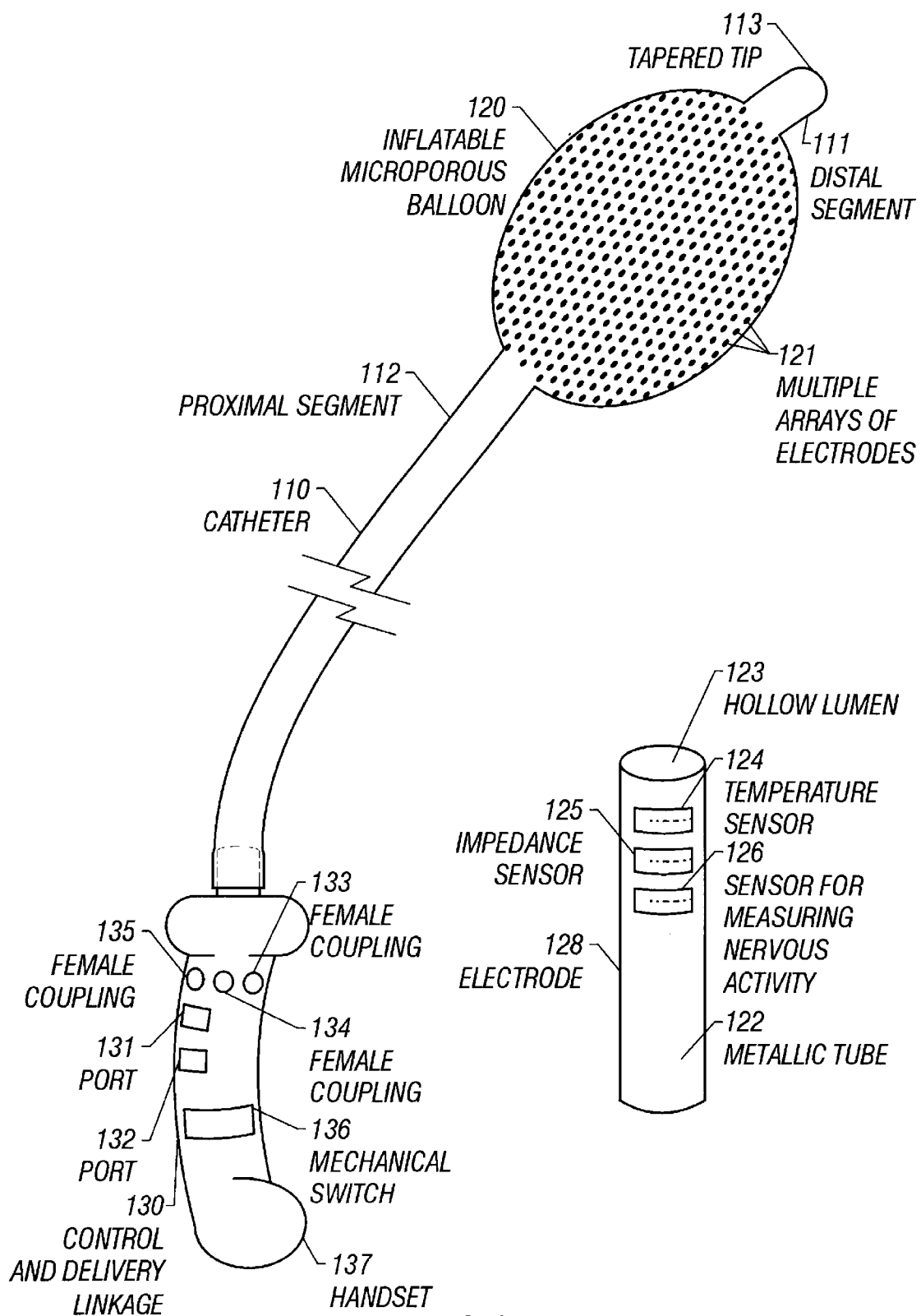
FIG. 1 is a diagram of a system for ablating tissue using a catheter and electrode assembly.

FIG. 1 is a block diagram of a system for ablating tissue associated with the circulatory, respiratory, reproductive, digestive, auditory and urinary systems along with their related sphincters and associated musculature using a catheter and electrode assembly.

A catheter and electrode assembly 100 for treating tissue includes a catheter 110, an inflatable microporous balloon 120 and a control and delivery linkage 130.

The catheter 110 includes a short, distal segment 111 and a proximal segment 112. The distal segment includes a tapered tip 113 for easy insertion into an orifice or surgically created opening. The tapered tip 113 may be either flexible or rigid depending upon the orifice or opening into which the catheter 110 is to be inserted. The overall length of the shaft of the catheter 110 (including the inflatable, microporous balloon 120) from the tapered tip 113 to the junction where the catheter 110 is coupled to the control and delivery linkage 130 is about 65 centimeters. The diameter of the catheter 110 is about 0.4 centimeters. In an alternative embodiment, the length and diameter of the shaft of the catheter 110 may vary substantially depending upon application.

Taken together, the distal segment 111, the inflatable, microporous balloon 120 and the proximal segment 112 are linearly contiguous and form one continuous unit.

The inflatable microporous balloon 120 includes multiple arrays of regularly positioned electrodes 121 embedded into the wall of the balloon. Each electrode 128 includes a metallic tube 122 defining a hollow lumen 123, a temperature sensor 124 an impedance sensor 125 and a sensor for measuring nervous activity. In addition to ablating tissue by delivering RF energy, the electrodes are disposed to deliver at least one flowable substance to the area where ablation is to take place. In a preferred embodiment, the flowable substance includes saline with a concentration of less than about 10% NaCl, which aids in hydration of body structures. However, in alternative embodiments, the deliverable, flowable liquids include other substances, including anesthetic drugs, anti-inflammatory agents, chemotherapeutic agents, systemic or topical antibiotics, collagen and radioactive substances such as labeled traces. In alternative embodiments, the overall dimensions of the inflatable microporous balloon 120 can vary as long as they are responsive to the dimensions of the targeted tissue. For instance, the dimensions of an inflatable, microporous balloon 120 that is used to ablate tissue in a uterus will be larger than those of an inflatable microporous balloon that is used to ablate tissue in a fallopian tube. In other alternative embodiments, the shape and length of the electrodes may vary.

Exact positioning of the electrodes 121, 128 is achieved through the use of visualization apparatus couple and by inflating the balloon 120. Inflation of the balloon 120 causes the embedded electrodes 121, 128 to be brought into contact with either a select portion or the entire surface of the targeted tissue.

Manipulating the control and delivery linkage 130 operates the assembly 100. The control and delivery linkage 130 includes a port 131, a second port 132, three female couplings 133, 134 and 135, a mechanical switch 136 and a handset 137.

The port 131 can be coupled to a source of RF energy. The port 132 can be coupled to visualization apparatus, such as fiber optic devices, fluoroscopy equipment and related endoscopic apparatus, to allow internal viewing of the targeted tissue. The female coupling 133 can be connected to a syringe or other dive to which positive pressure can be applied to inflate the balloon 120. In a preferred embodiment, female coupling 134 can be connected to biologically nonreactive tubing through which saline can be infused so that the saline can continually circulate through the microporous balloon 120 and the electrodes 121, 128. Female coupling 135 can be connected to drug administration apparatus. Mechanical switch 136 allows for the activation of individual electrodes in a manner, the manner including selecting any of number, sequence, pattern and position, that is responsive to the judgment of medical or veterinary personnel. The port 131, port 132, female couplings 133, 134, 135 and mechanical switch 136 are all located immediately adjacent to the handset 137 to allow easy operation.

First Method of Operation

Figure 2A:
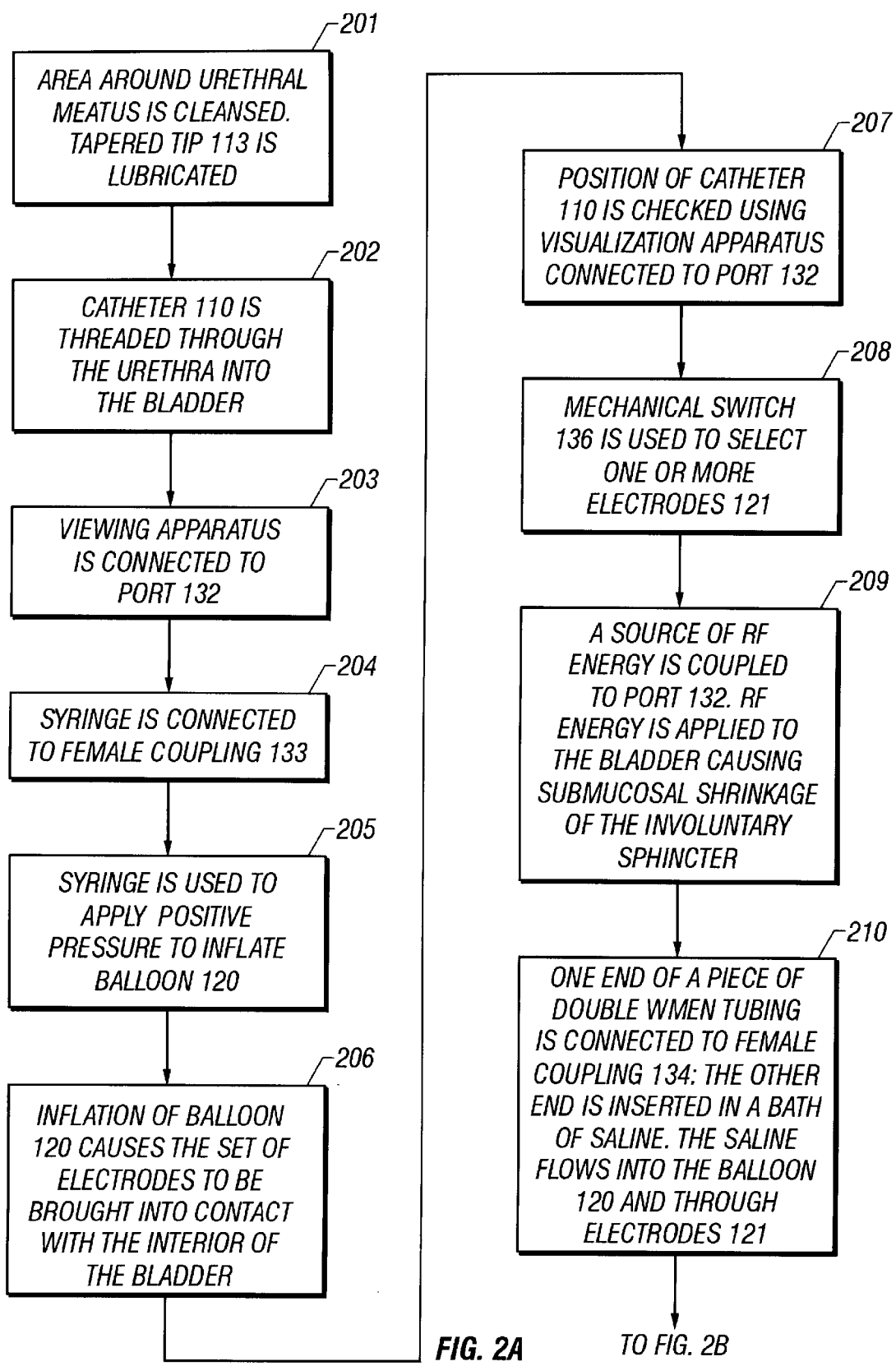
FIGS. 2A and 2B is a process flow diagram of a method for treatment for urinary incontinence in women.
Figure 2B:
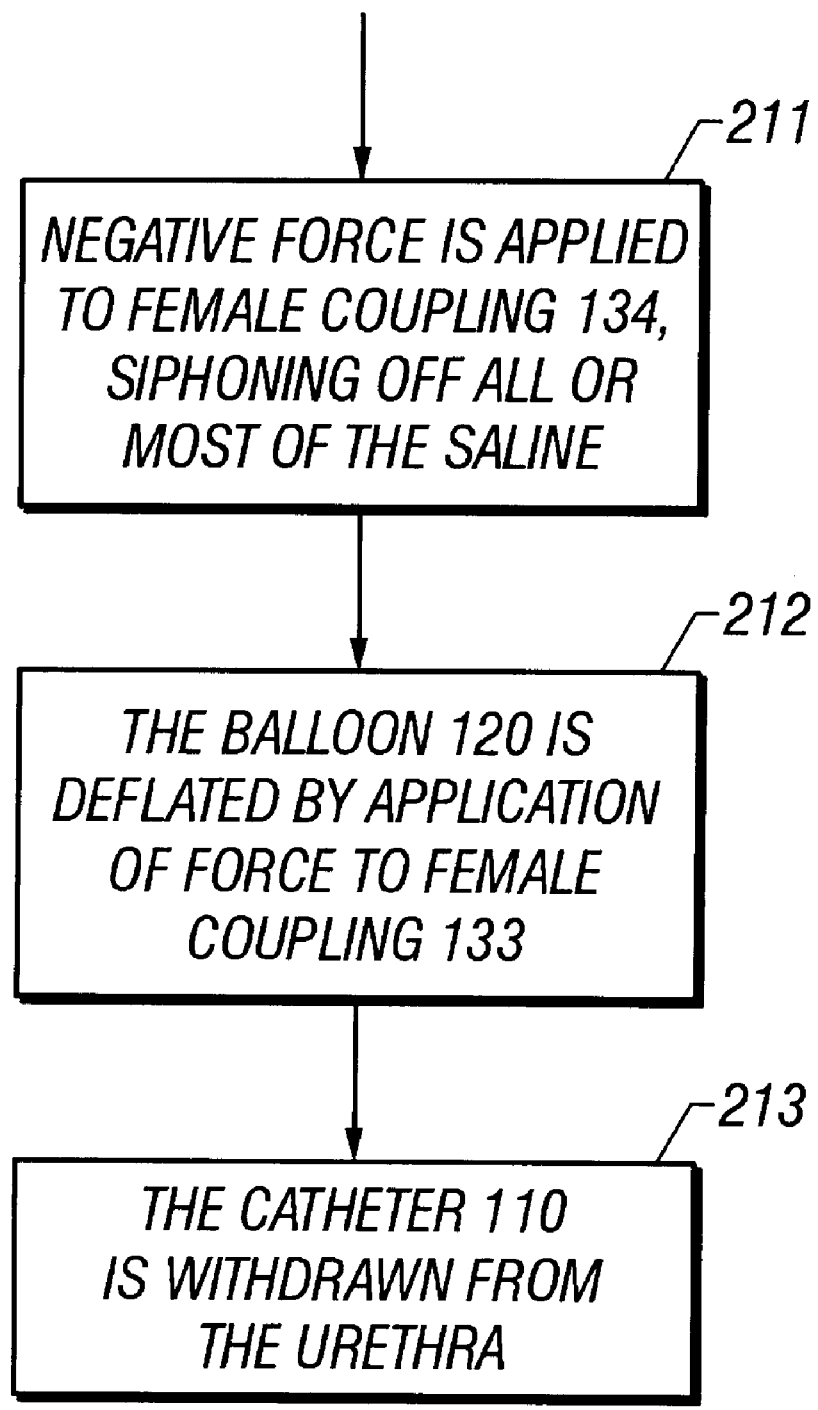

FIG. 2 is a process flow diagram of a method for treatment for urinary incontinence in women.

This method of operation is appropriate for the type of incontinence common to many post-menopausal parous women. In some women, the structure of the pelvic support of the bladder is damaged, either by parturition or urethral atrophy caused by estrogen deprivation. When this occurs, the urethra shortens, and the normal urethovesical angle is lost. The goals of this method of operation include producing uniform shrinkage of submuscosal tissue. This shrinkage helps restore the urethovesical angle that is important for closure of the urethral sphincter.

A method 200 is performed using a catheter and electrode assembly 100.

In a step 201, the area around the urethral meatus is cleansed. The tapered tip of the catheter 110 is well lubricated and introduced into the urethral meatus in an upward and backward direction, in much the same way one would introduce a Foley catheter. Due to the potential for inducing pain, the outer opening of the urethra may be pretreated with a topical anesthetic before insertion. The choice of pharmaceutical agents to be infused prior to or during treatment will be responsive to judgments by medical personnel and may include lubricants, anesthetics, antispasmodics, anti-inflammatories, antibiotics or other agents.

In a step 202, the catheter 110 is threaded through the urethra until the tapered tip 113 and the inflatable, microporous balloon 120 extend past the neck of the bladder. Strict aseptic technique is maintained during this step and all subsequent ones.

In a step 203, viewing apparatus coupled to port 132 is used to examine the interior of the bladder, evaluate the positioning of the catheter 110 and determine which areas of the submucosal tissue are targeted for ablation and shrinkage.

In a step 204, a syringe is connected to the female coupling 133 included in the control and delivery linkage 130.

In a step 205, the syringe is used to exert positive pressure and inflate the inflatable, microporous balloon 120 with air or liquid. Inflation of the balloon 120 serves several purposes. In addition to snugly positioning the electrode 121 against the wall of the bladder, the inflatable, microporous balloon 120 also helps anchor the catheter in place. In an alternative embodiment, a second balloon 120 is used to help seal off the bladder neck.

In a step 206, inflation of the balloon 123 causes the set of electrodes to be brought into contact with the interior of the bladder.

In a step 207, the position of the catheter and the balloon is checked again using the visual apparatus coupled through port 132. Any correction to the position of the catheter 110 is made at this time, by repeating steps 202 through 206.

In a step 208, one or more electrodes 121, 128 are selected for activation. Since the goal of treatment includes uniform shrinkage of the submucosal tissue, the selected electrodes 121, 128 usually adhere to a uniform pattern. The number and pattern of selected electrodes is responsive to judgment of medical personnel. The mechanical switch 136 is used to select one or more electrodes 121, 128.

In a step 209, a source of RF energy is applied to port 131. RF energy is provided to electrodes 121, 128 to shrink the targeted tissue. In a preferred embodiment, the RF energy has a frequency between 435 kilohertz and 485 kilohertz. The RF energy is received by the submucosal tissue immediately near the electrodes for period of time less than ten minutes. The duration of time and frequency of energy are responsive to judgments of medical personnel. Application of RF energy causes the involuntary sphincter to shrink so that urine does not seep through.

In a step 210, one end of a piece of biologically nonreactive double-lumen tubing is attached to female coupling 134; the other end of the tubing is attached to a pump which is submerged in a bath of saline or other flowable substance that is maintained at a constant temperature. The saline or flowable substance is drawn through the holes in the electrodes 128 and the micropores of the balloon 120, as needed, to lower the temperature of the region and prevent collateral thermal damage. Double lumen tubing permits constant circulation of the flowable substance throughout the bladder and balloon 120. The nature, temperature and amount of flowable substance are responsive to judgments by medical personnel.

In a step 211, all or most of the flowable liquid that has been circulating through the electrodes 128 and micropores of the balloon is siphoned off by the application of negative force to female coupling 137.

In a step 212, the inflatable, microporous balloon 120 is deflated by application of negative pressure on the syringe connected to female coupling 133.

In a step 213, the catheter 110 is withdrawn from the urethra.

Second Method of Operation

Figure 3A:
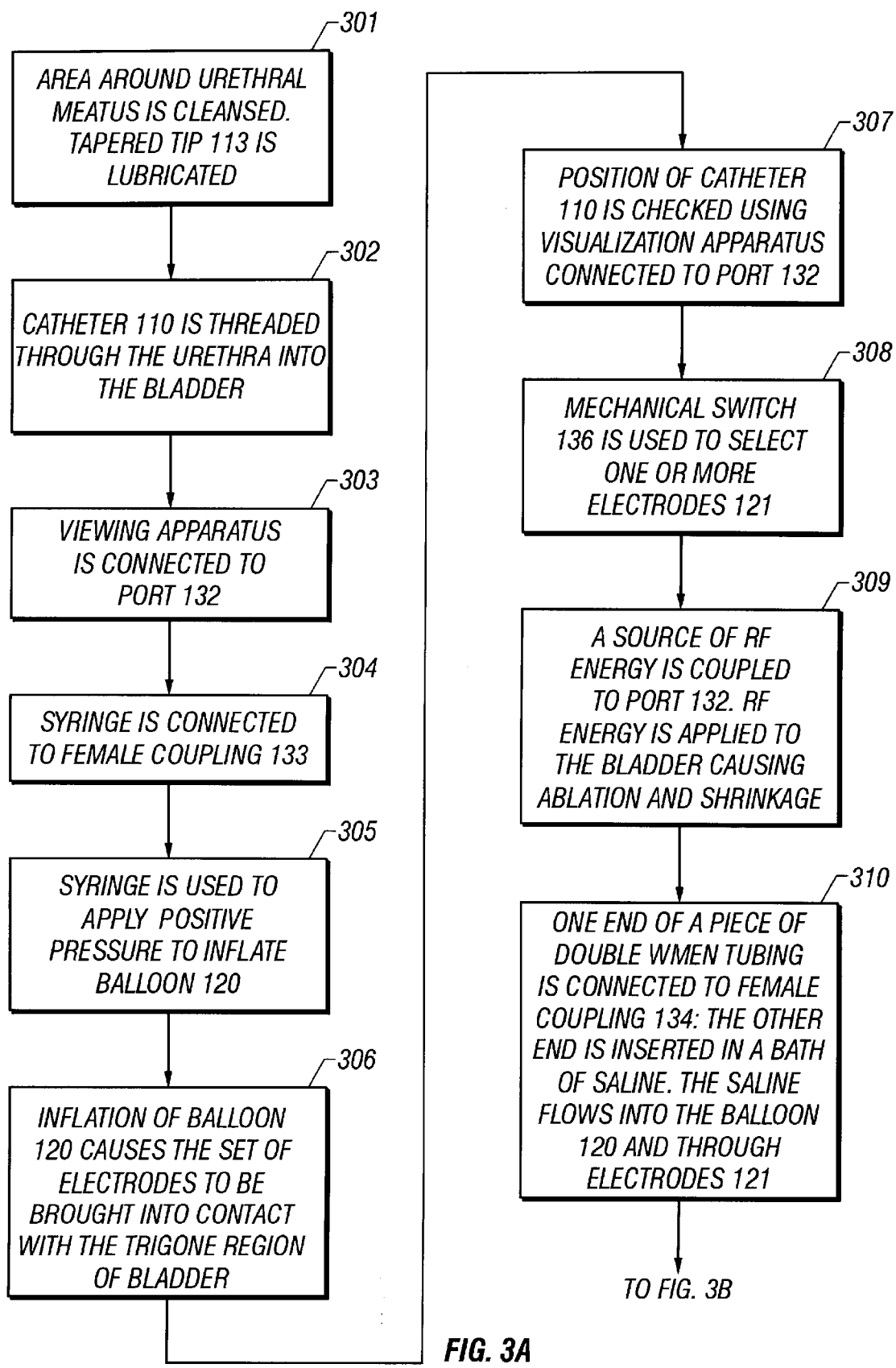
FIGS. 3A and 3B is a process flow diagram of a method for another treatment of urinary incontinence in women.
Figure 3B:
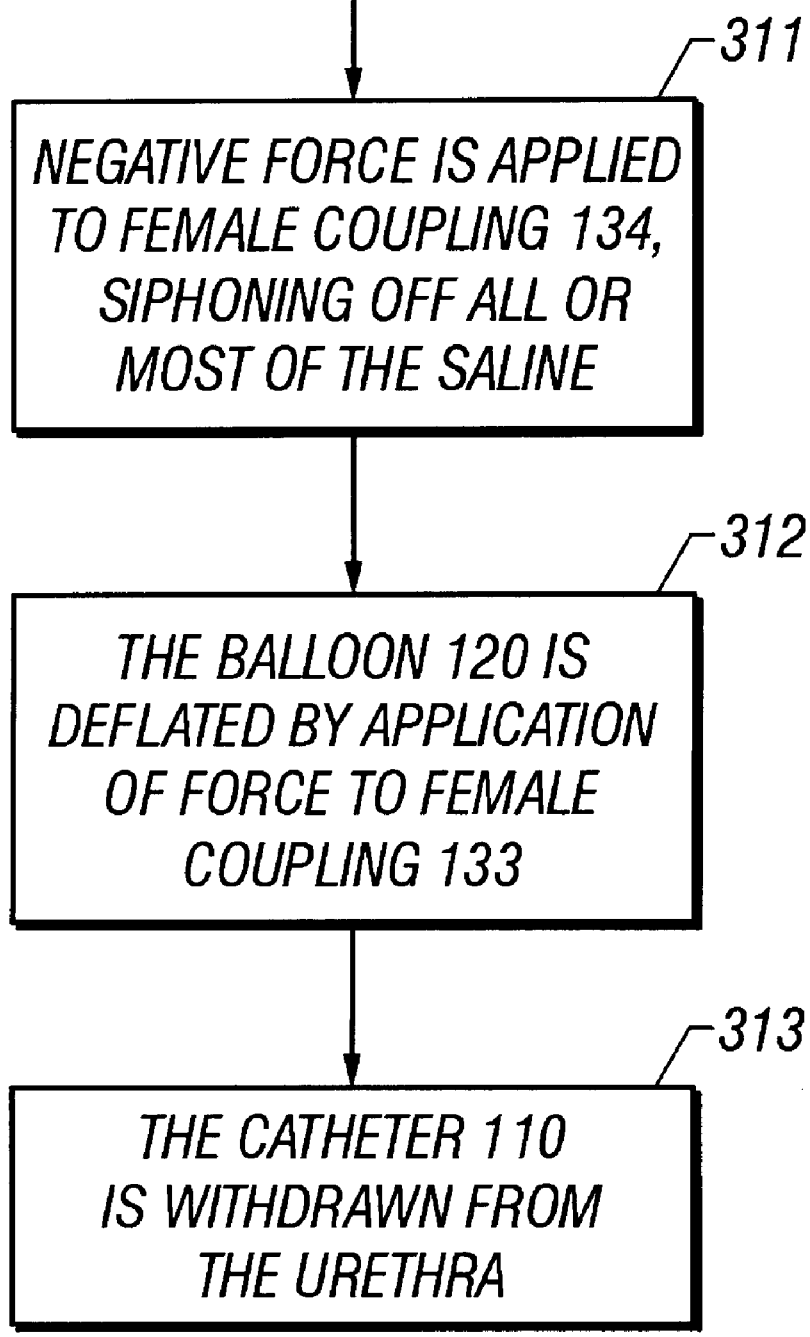

FIG. 3 is a process flow diagram of a method for another treatment for urinary incontinence in women.

This method of treatment is appropriate when incontinence is caused by inflammatory lesions of the muscosal tissue in the trigone area of the bladder. These lesions can cause uncontrollable detrusor contractions and unwanted passage of urine, often called urgency incontinence. The goals of this method include shrinkage of muscosal tissue and ablation of the lesions causing incontinence.

A method 300 is performed using a catheter and electrode assembly 100.

In a step 301, the area around the urethral meatus is cleansed. The tapered tip of the catheter 110 is well lubricated and introduced into the urethral meatus in an upward and backward direction, in much the same way one would introduce a Foley catheter. Due to the potential for inducing pain, the outer opening of the urethra may be pretreated with a topical anesthetic before insertion. The choice of pharmaceutical agents to be infused prior to or during treatment will be responsive to judgments by medical personnel and may include lubricants, anesthetics, antispasmodics, anti-inflammatories, antibiotics or other agents.

In a step 302, the catheter 110 is threaded through the urethra until the tapered tip 113 and the inflatable, microporous balloon 120 extend past the neck of the bladder until the balloon 120 is in proximate contact with the trigone area of the bladder. Strict aseptic technique is maintained during this step and all subsequent ones.

In a step 303, viewing apparatus coupled to port 132 is used to examine the interior of the bladder, search for lesions in the trigone area, evaluate the positioning of the catheter 110 and determine which areas of the mucosal tissue are targeted for ablation and shrinkage.

In a step 304, a syringe is connected to the female coupling 133 included in the control and delivery linkage 130.

Figure 12:
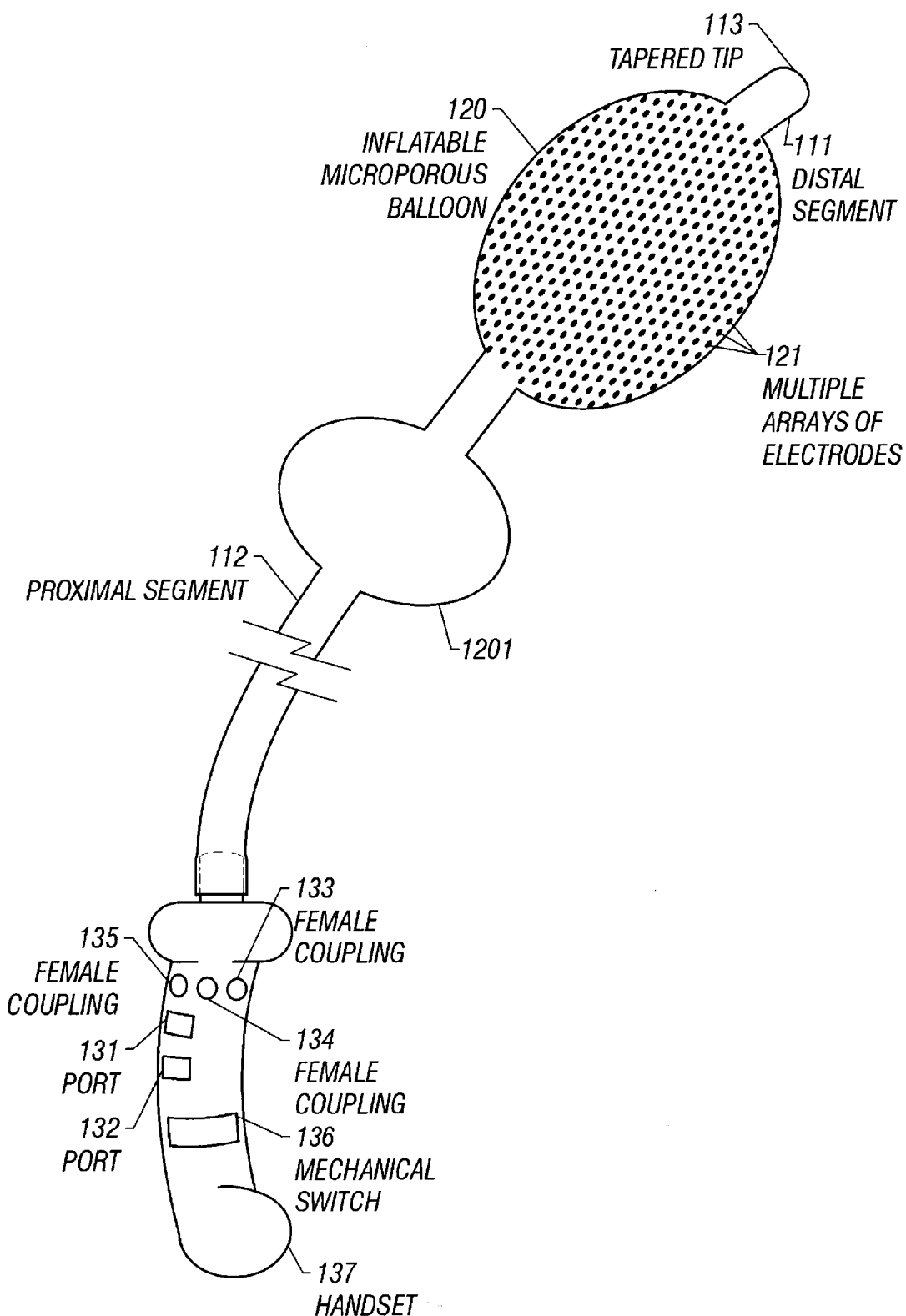
FIG. 12 is a diagram of an alternative embodiment of the system of FIG. 1.

In a step 305, the syringe is used to exert positive pressure and inflate the inflatable, microporous balloon 120 with air or liquid. Inflation of the balloon 120 serves several purposes. In addition to snugly positioning the electrodes 121, 128 against the trigone area of the bladder, the inflatable microporous balloon 120 also helps anchor the catheter in place. In an alternative embodiment, a second balloon 1201 (FIG. 12) serves as a blocking element used to help seal off the bladder neck.

In a step 306, inflation of the balloon 120 causes the set of electrodes to be brought into contact with most or all of the entire interior of the bladder wall, including the offending lesions of the trigone area.

In a step 307, the position of the catheter and the balloon is checked once again using the visual apparatus coupled through port 132. Any correction to the position of the catheter 110 is made at this time, by repeating steps 302 through 306.

In a step 308, one or more electrodes 121, 128 are selected for activation. Since the goals of treatment include uniform shrinkage of the mucosal tissue, the selected electrodes 121, 128 usually adhere to a uniform pattern. In some instances it may be desirable to shrink other interior areas of the bladder as well. In such instances, additional electrodes 121, 128 may be selected for activation. The number and pattern of selected electrodes is responsive to the judgments of medical or veterinary personnel. The mechanical switch 136 is used to select one or more electrodes 121, 128.

In a step 309, a source of RF energy is applied to port 131. RF energy is provided to electrodes 121, 128 to shrink the targeted tissue. In a preferred embodiment, the RF energy has a frequency between 435 kilohertz and 485 kilohertz. The RF energy is received by the submucosal tissue immediately near the electrodes for period of time less than ten minutes. The duration of time and frequency of energy are responsive to judgments of medical personnel. Application of RF energy causes the involuntary sphincter to shrink so that urine does not seep through.

In a step 310, one end of a piece of biologically nonreactive double-lumen tubing is attached to female coupling 134; the other end of the tubing is attached to a pump which is submerged in a bath of saline or other flowable substance that is maintained at a constant temperature. The saline or flowable substance is drawn through the holes in the electrodes 128 and the micropores of the balloon 120, as needed, to lower the temperature of the region and prevent collateral thermal damage. Double lumen tubing permits constant circulation of the flowable substance throughout the bladder and balloon 120. The nature, temperature and amount of flowable substance are responsive to judgments by medical personnel.

In a step 311, all or most of the flowable liquid that has been circulating through the electrodes 128 and micropores of the balloon is siphoned off by the application of negative force to female coupling 137.

In a step 312, the inflatable, microporous balloon 120 is deflated by application of negative pressure on the syringe connected to female coupling 133.

In a step 313, the catheter 110 is withdrawn from the urethra.

Third Method of Operation

Figure 4B:
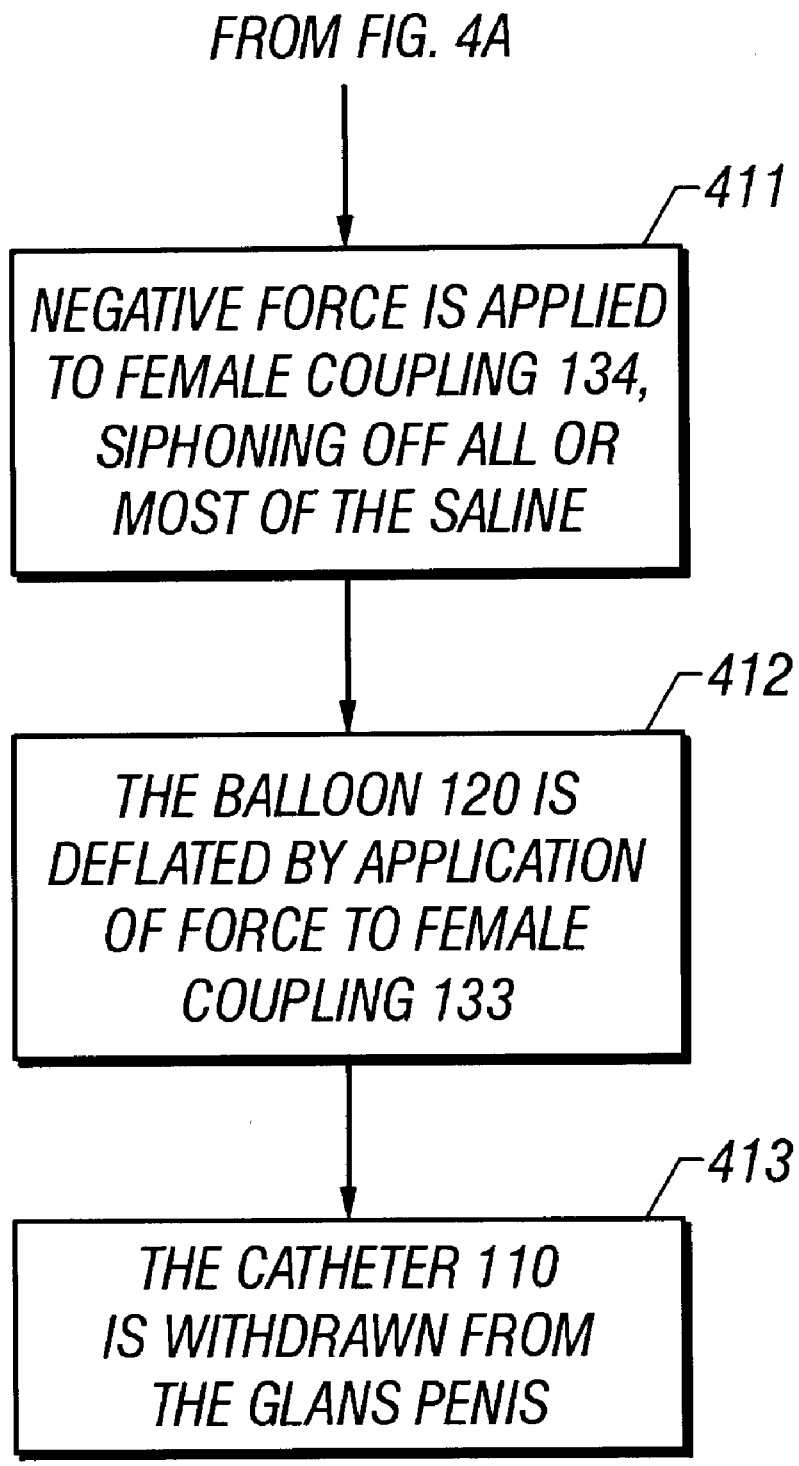

FIG. 4 is a process flow diagram of a method for treatment of incontinence in men.

Presently, incontinence in men accounts for only 15% of all adult incontinence. It is usually secondary to prostatic surgery for benign prostatic hypertrophy or prostatic carcinoma. If surgical damage to the external sphincter has been inflicted, complete incontinence can result. The goals of this method of operation include removing lesions caused by prostatic surgery, shrinking the sphincter, and resorting the urethovesical angle.

A method 400 is performed using a catheter and electrode assembly 100.

In a step 401, the tapered tip 113 of the catheter 110 is well lubricated. The area of the glans penis around the urinary meatus is washed with a cleansing agent such as benzalonium chloride. Due to the potential for inducing pain, the area surrounding the urinary meatus may be pretreated with a topical anesthetic before insertion; depending upon the circumstances, a muscle relaxant may be indicated.

The preferred size of the catheter 110 will be responsive to the orifice through which the catheter is inserted. The choice of pharmaceutical agents to be infused prior to or during treatment will be responsive to judgments by medical or veterinary personnel, and may include lubricants, anesthetics, antispasmodics, antiinflammatories, antibiotics or other agents.

In a step 402, the catheter 110 is introduced into the urethra along the anterior wall. The catheter is advanced approximately 17.5–25 centimeters. Since the length from the bladder to the end of the glans penis varies, the distance that the catheter is advanced is responsive to the judgment of medical or veterinary personnel.

In a step 403, viewing apparatus coupled to the port 132 may be used to examine both the voluntary and involuntary sphincter for evidence of lesions or other damage caused by prior surgery. The viewing apparatus is also used to evaluate the urethrovesical angle, position the catheter 110 and balloon 120, and determine which areas are candidates for ablation and shrinkage.

In a step 404, a syringe is connected to the female coupling 133 included in the control and delivery linkage 130.

In a step 405, the syringe is used to exert positive pressure and inflate the inflatable, microporous balloon 120 with air or liquid. Inflation of the balloon 120 serves several purposes. In addition to snugly positioning the electrodes 121, 128, the inflatable microporous balloon 120 also helps anchor the catheter in place. In an alternative embodiment, a second balloon 1201 (FIG. 12) is used to help seal off the bladder neck.

In a step 406, inflation of the balloon 120 causes the set of electrodes to be brought into contact with the interior of the bladder.

In a step 407, the position of the catheter and balloon is checked again using the visual apparatus coupled through port 132. Any correction to the position of the catheter 110 is made at this time by repeating steps 402 through 406.

In a step 408, one or more electrodes 121, 128 are selected for activation. Since the goals of treatment include uniform shrinkage of the sphincter, the selected electrodes 121, 128 usually adhere to a uniform pattern. In some instances it may be desirable to shrink other interior areas of the bladder as well. In such instances, additional electrodes 121, 128 may be selected for activation. The number and pattern of selected electrodes is responsive to the judgments of medical or veterinary personnel. The mechanical switch 136 is used to select one or more electrodes 121, 128.

In a step 409, a source of RF energy is coupled to port 13. RF energy is provided to the electrodes so as to ablate the targeted portions of the bladder. In a preferred embodiment, the RF energy has a frequency between 435 kilohertz and 485 kilohertz. The RF energy is received by the tissue immediately near the electrodes. The tissue is heated for a short period of time until ablation occurs. Application of RF energy has the effect of ablating the offending lesions and shrinking the involuntary sphincter. This shrinkage results in repositioning of the urethrovesical angle in such a way that that urine does not seep through the sphincter.

In a step 410, one end of a piece of biologically nonreactive double-lumen tubing is attached to female coupling 134; the other end of the tubing is attached to a pump which is submerged in a bath of saline or other flowable substance that is maintained at a constant temperature. The saline or flowable substance is drawn through the holes in the electrodes 128 and the micropores of the balloon 120, as needed, to lower the temperature of the region and prevent collateral thermal damage. Double lumen tubing permits constant circulation of the flowable substance throughout the bladder and balloon 120. The nature, temperature and amount of flowable substance are responsive to judgments by medical personnel.

In a step 411, all or most of the flowable liquid that has been circulating through the electrodes 128 and micropores of the balloon is siphoned off by the application of negative force to female coupling 137.

In a step 412, the inflatable, microporous balloon 120 is deflated by application of negative pressure on the syringe connected to female coupling 133.

In a step 413, the catheter 110 and inflatable, microporous balloon 120 is withdrawn from the urethra.

Fourth Method of Operation

Figure 5A:
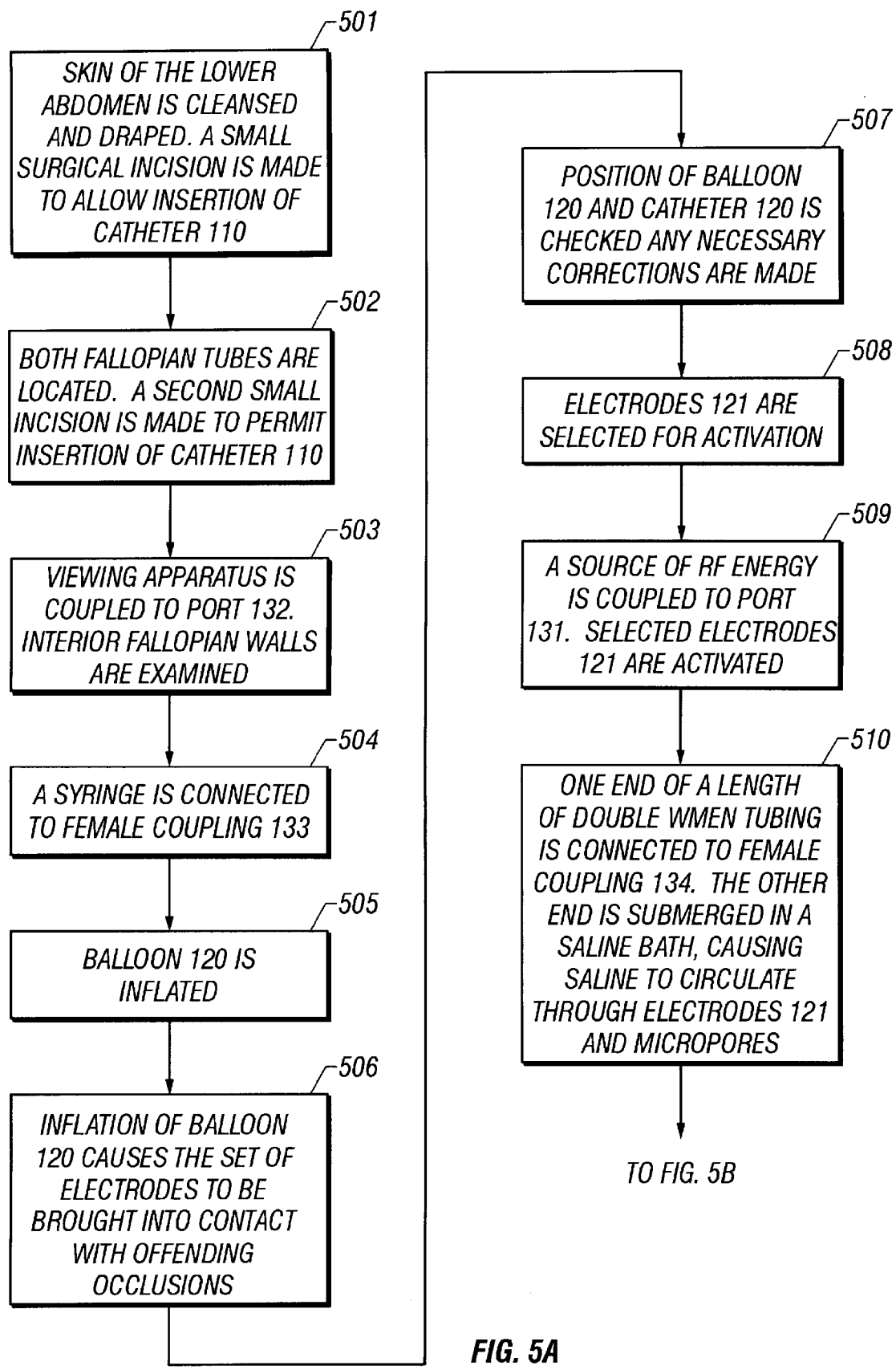
FIGS. 5A and 5B is a process flow diagram of a method for treatment of an occluded fallopian tube.
Figure 5B:
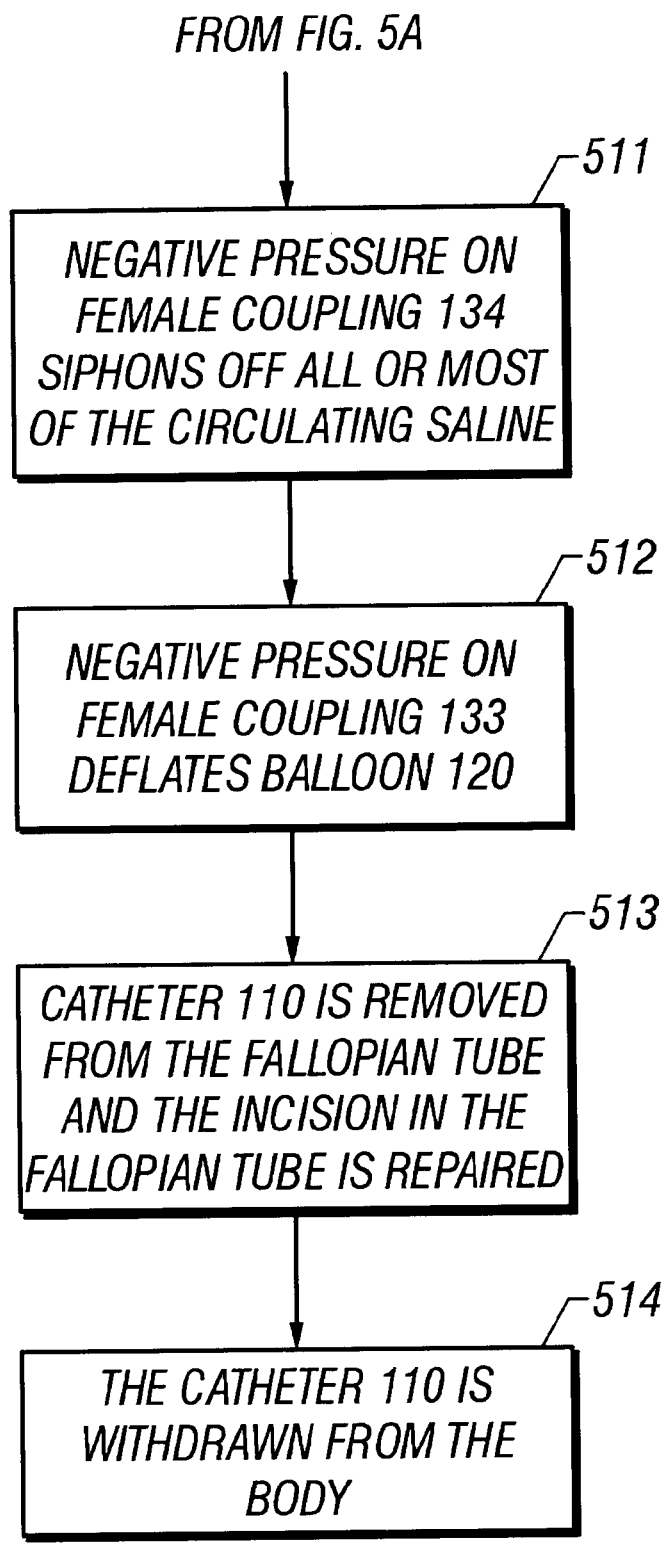

FIG. 5 is a process flow diagram for a method of treating an occluded fallopian tube.

Blockage of the fallopian tube is a frequent cause of infertility in women of reproductive years. Diagnosis of tubal blockage is generally made by hysteroslpingogram and diagnostic laparoscopy. The goals of this method of treatment include restoration of the fallopian tube patency.

A method 500 is performed using a catheter and electrode assembly 100.

In a step 501, the skin of the lower abdomen is cleansed and draped. A small surgical incision is made to allow the insertion of the catheter 110. Strict aseptic technique is maintained during this step and all subsequent ones. Due to the potential for inducing pain, the surface of the skin may be pretreated with a topical anesthetic before insertion. A mild anesthetizing agent such as VerSed may be indicated.

The choice of pharmaceutical agents to be infused prior to or during treatment will be responsive to judgments by medical or veterinary personnel and may include lubricants, anesthetics, antispasmodics, anti-inflammatories, antibiotics or other agents.

In a step 502, both fallopian tubes are located. A second small incision is made in the wall of one the fallopian tubes to permit insertion of the catheter 110. Care is taken not to abrade the ovaries or damage the broad ligament that supports the fallopian tube.

In a step 503, viewing apparatus coupled to port 132 is used to examine the interior walls of the fallopian tube, search for occlusions, evaluate the position of the catheter 110 and balloon 120, and determine which areas are targeted for ablation.

In a step 504, a syringe is connected to the female coupling 133 included in the control and delivery linkage 130.

In a step 505, the syringe is used to exert positive pressure and inflate the inflatable, microporous balloon 120 with air or liquid. Inflation of the balloon 120 serves several purposes. First, in some instances, it is possible that simple inflation of the balloon will be sufficient to dilate an occluded region. Inflation of the balloon 120 also causes the electrodes 121, 128 to be positioned snugly against the walls of the fallopian tube. Moreover, the inflatable microporous balloon 120 also helps anchor the catheter in place.

In a step 506, inflation of the balloon 120 causes the set of electrodes to be brought into contact with the offending occlusions and blockages.

In a step 507, the position of the catheter and the balloon is checked once again using the visual apparatus coupled through port 132. Any correction to the position of the catheter 110 is made at this time, by repeating steps 503 through 506.

In a step 508, one or more electrodes 121, 128 are selected for activation. Unlike the previous methods, the selected electrodes 121, 128 need not adhere to a uniform pattern. The number and pattern of selected electrodes is responsive to the judgments of medical or veterinary personnel.

In a step 509, a source of RF energy is applied to port 131. RF energy is provided to electrodes 121, 128 to shrink the targeted tissue. In a preferred embodiment, the RF energy has a frequency between 435 kilohertz and 485 kilohertz. The RF energy is received by the tissue immediately near the electrodes for period of time less than ten minutes. The duration of time and frequency of energy are responsive to judgments of medical personnel.

In a step 510, one end of a piece of biologically nonreactive double-lumen tubing is attached to female coupling 134; the other end of the tubing is attached to a pump which is submerged in a bath of saline or other flowable substance that is maintained at a constant temperature. The saline or flowable substance is drawn through the holes in the electrodes 128 and the micropores of the balloon 120, as needed, to lower the temperature of the region and prevent collateral thermal damage. Double lumen tubing permits constant circulation of the flowable substance throughout the bladder and balloon 120. The nature, temperature and amount of flowable substance are responsive to judgments by medical or veterinary personnel.

In a step 511, all or most of the flowable liquid that has been circulating through the electrodes [121] 128 and micropores of the balloon is siphoned off by the application of negative force to female coupling 137.

In a step 512, the inflatable, microporous balloon 120 is deflated by application of negative pressure on the syringe connected to female coupling 133.

In a step 513, the catheter 110 is removed from the fallopian tube and the incision in the fallopian tube is repaired.

In a step 514, the catheter 110 is withdrawn from the incision where it was initially introduced into the body.

Steps 501 through 514 may be repeated, if necessary, to treat occlusions on the other fallopian tube.

Fifth Method of Operation

Figure 6B:
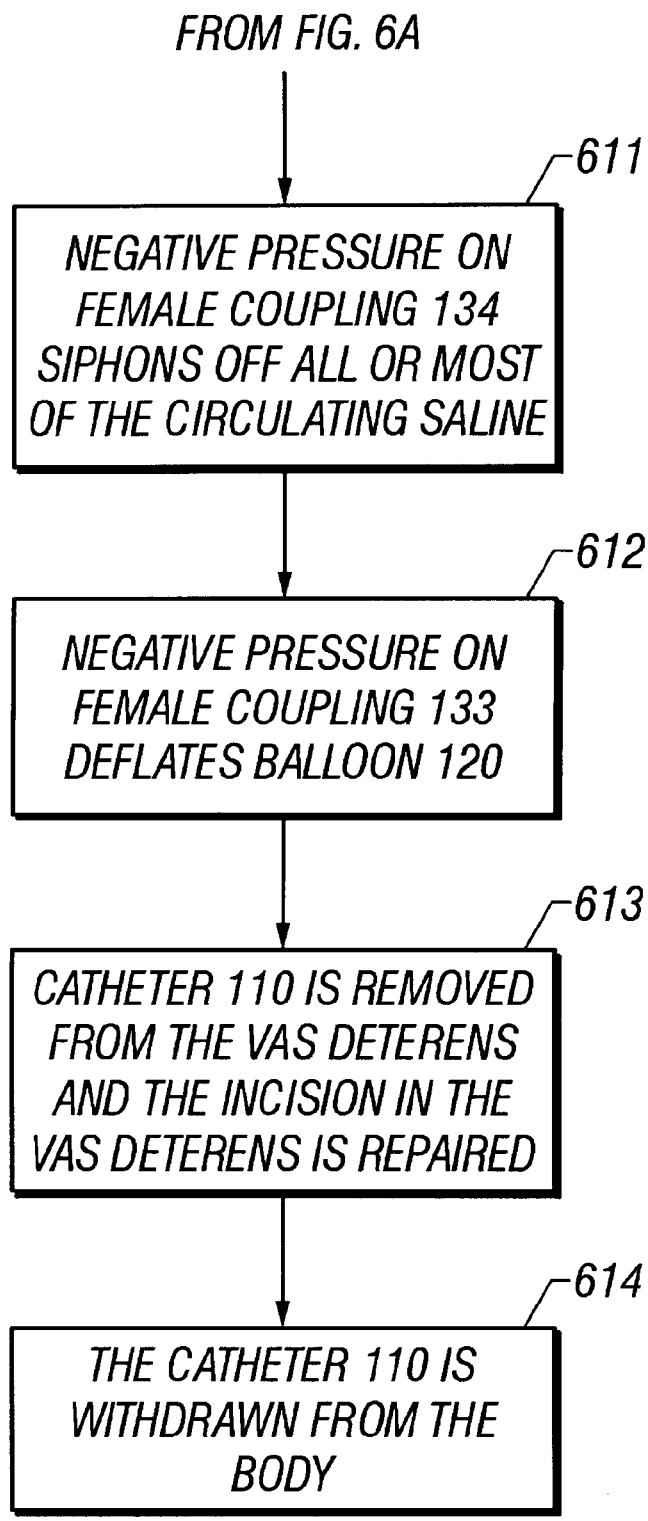

FIG. 6 is a process flow diagram of a method for treatment of an occluded vas deferens.

Obstruction of the vas deferens accounts for about 3% of male infertility. Obstruction may be congenital or acquired. Congenital obstruction may be an isolated abnormality or may be associated with cystic fibrosis. Acquired obstruction of the vas deferens may be caused by tuberculosis and gonorrhea. The goals of the method of operation include removal of the obstruction and restoration of fertility.

A method 600 is performed using a catheter and electrode assembly 100.

In a step 601, the skin of the lower abdomen is cleaned and draped. A small surgical incision is made to allow the insertion of the catheter 110. Strict aseptic technique is maintained during this step and all subsequent ones. Due to the potential for inducing pain, the surface of the skin may be pretreated with a topical anesthetic before insertion. A mild anesthetizing agent such as VerSed may be indicated. The choice of pharmaceutical agents to be infused prior to or during treatment will be responsive to judgments by medical personnel and may include lubricants, anesthetics, antispasmodics, anti-inflammatories, antibiotics or other agents.

In a step 602, both of the vas deferens are located. A second small incision is made into the wall of one the vas deferens to permit insertion of the catheter 110. Care is taken not to abrade the seminal vesicles or supporting structures.

In a step 603, viewing apparatus coupled to port 132 is used to examine the interior walls of the vas deferens, search for occlusions, evaluate the position of the catheter 110 and balloon 120, and determine which areas are targeted for ablation.

In a step 604, a syringe is connected to the female coupling 133 included in the control and delivery linkage 130.

In a step 605, the syringe is used to exert positive pressure and inflate the inflatable, microporous balloon 120 with air or liquid. Inflation of the balloon 120 serves several purposes. First, in some instances, it is possible that simple inflation of the balloon will be sufficient to dilate an occluded region. However, if this is not sufficient, inflation of the balloon 120 also causes the electrodes 121, 128 to be positioned snugly against the walls of the vas deferens. Moreover, the inflatable microporous balloon 120 also helps anchor the catheter in place.

In a step 606, inflation of the balloon 120 causes the set of electrodes to be brought into contact with the offending occlusions and blockages.

In a step 607, the position of the catheter and the balloon is checked once again using the visual apparatus coupled through port 132. Any correction to the position of the catheter 110 is made at this time, by repeating steps 603 through 606.

In a step 608, one or more electrodes 121, 128 are selected for activation. Unlike the previous methods, the selected electrodes 121, 128 need not adhere to a uniform pattern. The number and pattern of selected electrodes is responsive to the judgments of medical or veterinary personnel. The mechanical switch 136 is used to select one or of the electrodes 121, 128.

In a step 609, a source of RF energy is applied to port 131. RF energy is provided to electrodes 121, 128 to shrink the targeted tissue. In a preferred embodiment, the RF energy has a frequency between 435 kilohertz and 485 kilohertz. The RF energy is received by the tissue immediately near the electrodes for period of time less than ten minutes. The duration of time and frequency of energy are responsive to judgments of medical personnel. Application of RF energy has the effect of ablating the offending occlusions.

In a step 610, one end of a piece of biologically nonreactive double-lumen tubing is attached to female coupling 134; the other end of the tubing is attached to a pump which is submerged in a bath of saline or other flowable substance that is maintained at a constant temperature. The saline or flowable substance is drawn through the holes in the electrodes 128 and the micropores of the balloon 120, as needed, to lower the temperature of the region and prevent collateral thermal damage. Double lumen tubing permits constant circulation of the flowable substance throughout the bladder and balloon 120. The nature, temperature and amount of flowable substance are responsive to judgments by medical or veterinary personnel.

In a step 611, all or most of the flowable liquid that has been circulating through the electrodes 128 and micropores of the balloon is siphoned off by the application of negative force to female coupling 137.

In a step 612, the inflatable, microporous balloon 120 is deflated by application of negative pressure on the syringe connected to female coupling 133.

In a step 613, the catheter 110 is removed from the vas deferens and the incision in the wall of the vas deferens is repaired.

In a step 614, the catheter 110 is withdrawn from the incision where it was initially introduced into the body.

In a step 615, the incision where the catheter 110 was introduced is repaired.

Steps 601 through 615 may be repeated, if necessary, to treat occlusions on the remaining vas deferens.

Sixth Method of Operation

Figure 7:
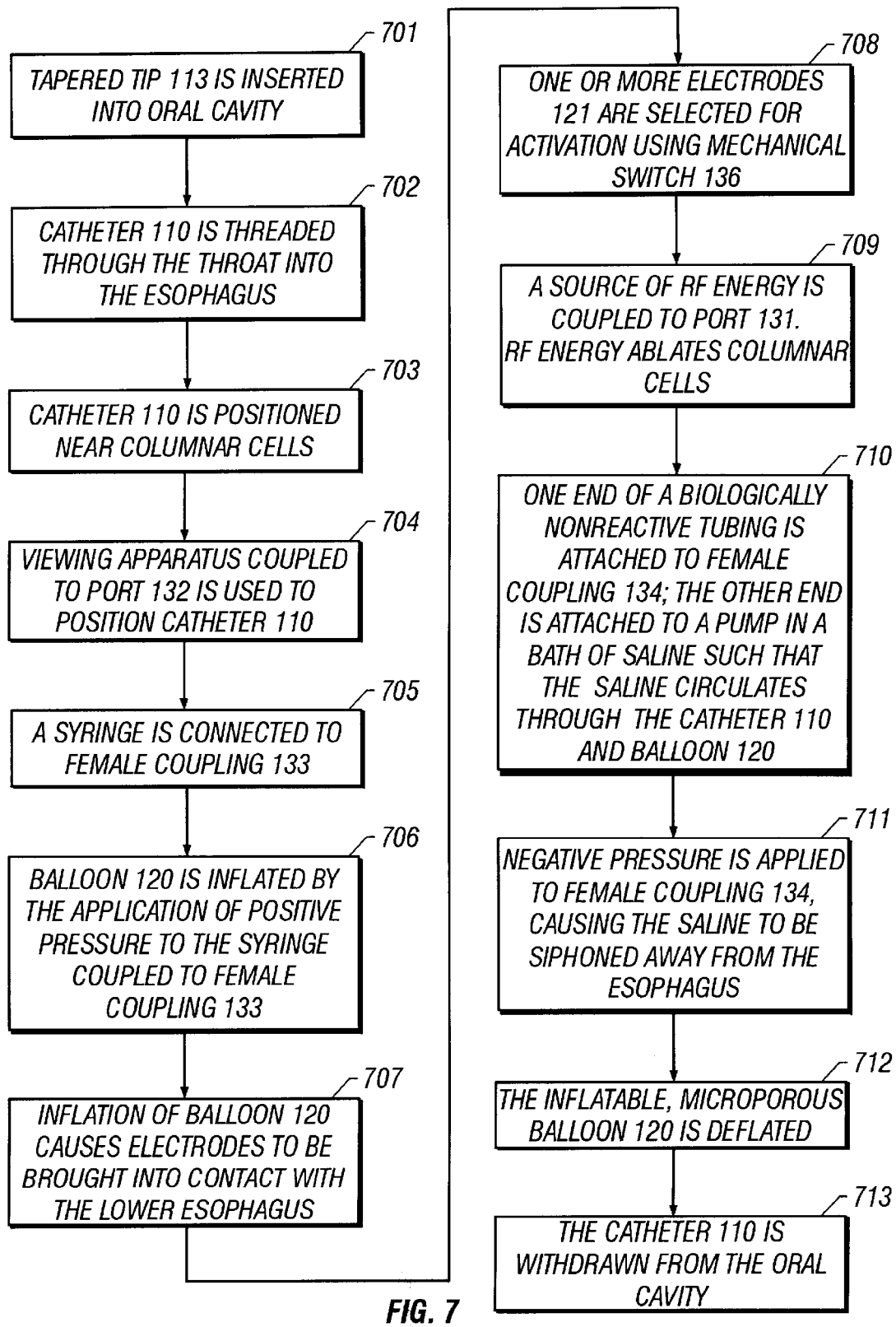
FIG. 7 is a process flow diagram of a method for treatment of Barrett's esophagus.

FIG. 7 is a process flow diagram of a method for treatment of Barrett's esophagus.

Barrett's esophagus often accompanies gastroesophegeal reflux disorder. It is diagnosed by esophagoscopy, which reveals the presence of columnar cell lining the lower esophagus. Adjacent peptic strictures may or may not coincide. Patients with Barrett's esophagus require close follow-up because these abnormal tissues often develop into adenocarcinoma.

In a step 701, the tapered tip 113 of the catheter 110 is inserted into the oral cavity. Due to the potential for inducing pain or a gag reflex, the oral cavity is preferably pretreated with lidocaine spray or other topical anesthetic before insertion; depending upon the circumstances, a muscle relaxant may be indicated. In an alternative embodiment, the tapered tip 113 of the catheter 110 is inserted into a surgically created stoma.

The preferred size of the catheter 110 will be responsive to the orifice through which the catheter is inserted. The choice of pharmaceutical agents to be infused prior to or during treatment will be responsive to judgments by medical personnel, and may include lubricants, anesthetics, antispasmodics, anti-inflammatories, antibiotics or other agents.

In a step 702, the catheter 110 is threaded through the throat into the lower esophagus. Precautions are preferably taken to ensure that the catheter 110 is not threaded through the trachea into the lungs.

In a step 703, the catheter 110 is positioned near the Barrett's esophagus.

In a step 704, viewing apparatus coupled to the port 132 may be used to position the catheter 110, examine the region, and determine which specific tissues are targeted for ablation. Healthy tissue composed of white squamous cells is distinguished from unhealthy pink columnar cells indicative of Barrett's esophagus.

In a step 705, a syringe is connected to the female coupling 133.

In a step 706, the syringe is used to exert positive pressure and inflate the balloon 120 with a flowable substance, such as air or liquid. Inflation of the balloon 120 serves several purposes. In addition to positioning the electrodes 121, 128, the balloon 120 also helps anchor the catheter 110 and prevents gas or liquids arising in the stomach from contaminating the region.

In a step 707, inflation of the balloon 120 causes the set of electrodes to be brought into contact with the interior of the lower esophagus.

In a step 708, one or more electrodes 121, 128 are selected for activation. Since the treatment goals include ablation of the columnar cells, electrodes that are proximate to these cells are selected. The mechanical switch 136 is used to select one more electrodes 121, 128.

In a step 709, A source of RF energy is coupled to port 131. RF energy is provided to the electrodes so as to ablate the targeted columnar cells. In a preferred embodiment, the RF energy has a frequency between 435 kilohertz and 485 kilohertz. The tissue immediately near the electrodes receives the RF energy. The strength and duration of time the energy is applied are responsive to judgments by medical personnel. In alternative embodiments, the electrodes may deliver other forms of energy, such as heat, microwaves, infrared or visible laser energy. In other alternative embodiments, the electrodes are controlled by a feedback technique using at least one sensor 126 such as an impedance or temperature sensor.

To perform ablation, the tissue is heated for a short period of time until ablation occurs. Application of RF energy causes cell death by dehydration or denaturation of cellular proteins.

To perform expansion, plumping, or shaping, the tissue is suffused with a flowable substance, such as a gas or liquid, a collagen, or another substance that can be absorbed by the body structure or tissue. The flowable substance can be exuded from the catheter, either using a separate flow line, or using the electrodes themselves. In a preferred embodiment, the tissue is heated for a short time, and thereafter cooled, so as to cause the flowable substance to crosslink or otherwise transform into a bulking, plumping, or shaping agent.

To perform coating, the flowable substance can be exuded so as to adhere to (or be adsorbed by) an epithelial layer of cells. In a preferred embodiment, the tissue is heated for a short time, and thereafter cooled, so as to cause the flowable substance to crosslink or otherwise transform into a solid mass coating or covering the epithelial layer.

To perform shrinking, the tissue is suffused with the flowable substance, with the flowable substance being selected so as to act as a receiving antenna or dielectric for the RF energy. RF energy is applied, which is differentially absorbed by the flowable substance; this causes the flowable substance to heat and to shrink the tissue it suffused, either by cell death, dehydration, or denaturation of cellular proteins.

In a step 710, one end of a piece of biologically nonreactive double-lumen tubing is attached to female coupling 134; the other end of the tubing is attached to a pump which is submerged in a bath of saline or other flowable substance that is maintained at a constant temperature. The saline or flowable substance is drawn through the holes in the electrodes 128 and the micropores of the balloon 120, as needed, to lower the temperature of the region and prevent collateral thermal damage. Double lumen tubing permits constant circulation of the flowable substance throughout the bladder and balloon 120. The nature, temperature and amount of flowable substance are responsive to judgments by medical or veterinary personnel.

In a step 711, all or most of the flowable liquid that has been circulating through the electrodes 128 and micropores of the balloon is siphoned off by the application of negative force to female coupling 137.

In a step 712, the inflatable microporous balloon is deflated by application of negative pressure on the syringe connected to female coupling 133.

In a step 713, the catheter 110 is withdrawn from the oral cavity. In an alternative embodiment, the catheter 110 is withdrawn from a stoma.

Seventh Method of Operation

Figure 8:
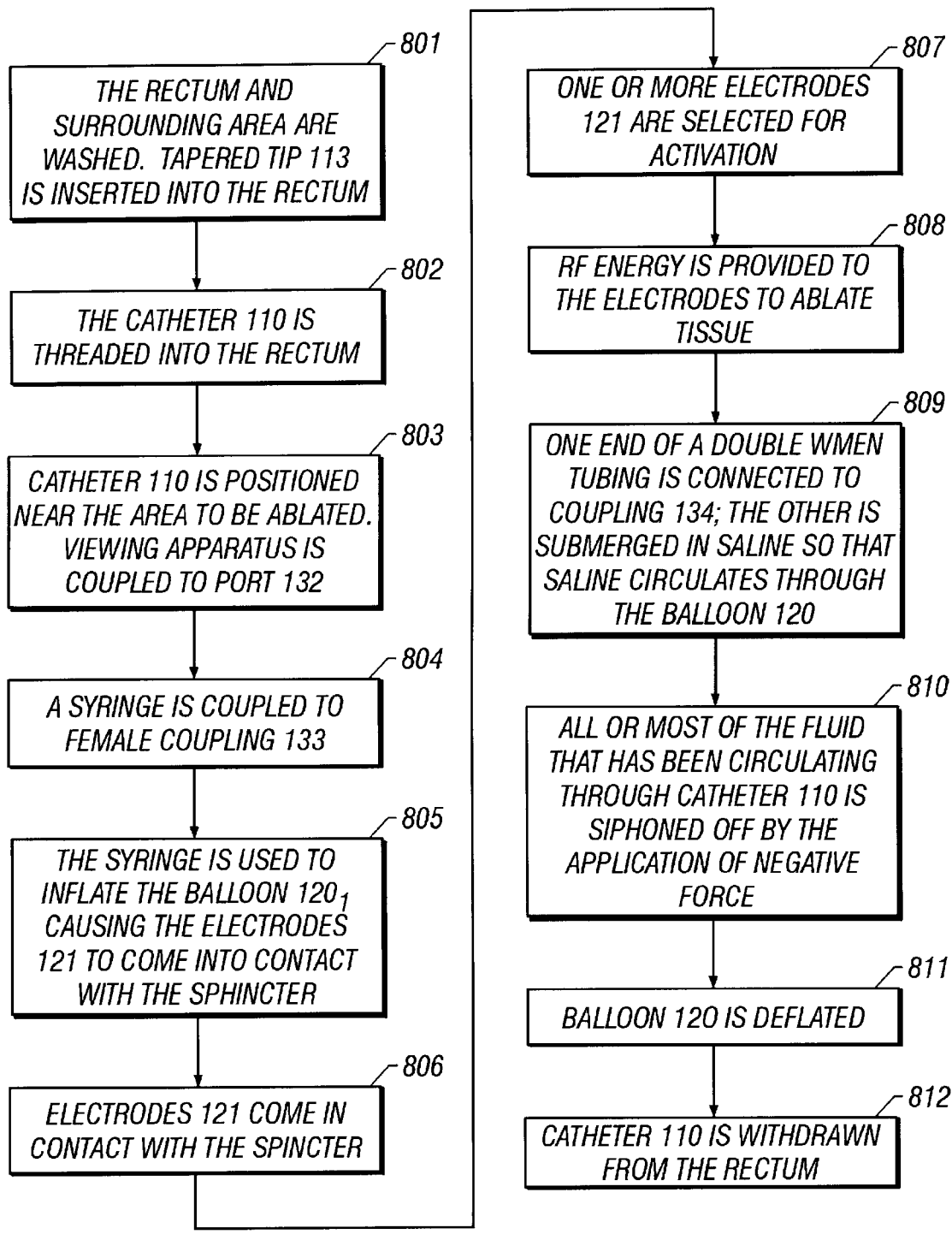
FIG. 8 is a process flow diagram for treatment of fecal incontinence.

FIG. 8 is a process flow diagram of a method for treatment of fecal incontinence.

A method 800 is performed using a catheter and electrode assembly 100. This method requires the use of four to eight electrodes and a blunt tapered tip 113.

In a step 801, the rectum and surrounding area are washed with a cleansing agent such as benzalonium chloride. A topical anesthetic may be applied to prevent pain associated with insertion; depending upon the circumstances, a muscle relaxant may be indicated. The tapered tip 113 of the catheter 110 is inserted into the rectum.

The preferred size of the catheter 110 will be responsive to the orifice through which the catheter is inserted. The choice of pharmaceutical agents to be infused prior to or during treatment will be responsive to judgments by medical personnel, and may include lubricants, anesthetics, antispasmodics, anti-inflammatories, antibiotics or other agents.

In a step 802, the catheter 110 is threaded into the rectum.

In a step 803, the catheter 110 is positioned near the area to be ablated. In the preferred embodiment, viewing apparatus such as an anoscope coupled to the port 132 may be used to examine the region and determine which specific tissues are targeted for ablation. It is important to distinguish between the voluntary and involuntary sphincter because fecal incontinence is frequently caused by defects in the involuntary sphincter.

In a step 804, a syringe is connected to the female coupling 133.

In a step 805, the syringe is used to exert positive pressure and inflate the inflatable, microporous balloon 120 with air or liquid. Inflation of the balloon 120 serves several purposes. In addition to positioning the electrodes 121, 128, the balloon also helps anchor the catheter 110 and prevents gas, liquid or fecal matter from contaminating the region. In an alternative embodiment, a second balloon is used to help seal off the area from contaminants.

In a step 806, inflation of the balloon 120 cause the set of electrodes to be brought into contact with the interior walls of the sphincter.

In a step 807, one or more electrodes 121, 128 are selected for activation. The number and pattern of selected electrodes is responsive to the judgment of medical or veterinary personnel. The mechanical switch 136 is used to select the electrodes 121, 128.

In a step 808, RF energy is provided to the electrodes so as to ablate the targeted tissue. In a preferred embodiment, the RF energy has a frequency between 435 kilohertz and 485 kilohertz. The RF energy is received by the tissue immediately near the electrodes. The tissue is heated for a short period of time until ablation occurs. Application of RF energy causes cell death by dehydration and denaturation of cellular proteins. The strength and duration of time the energy is applied are responsive to judgments by medical personnel. In alternative embodiments, the electrodes may deliver other forms of energy, such as heat, microwaves, infrared or visible laser energy. In other alternative embodiments, the electrodes are controlled by a feedback technique using at least one sensor 126 such as an impedance or temperature sensor.

In a step 809, one end of a piece of biologically nonreactive double-lumen tubing is attached to female coupling 134; the other end of the tubing is attached to a pump which is submerged in a bath of saline or other flowable substance that is maintained at a constant temperature. The saline or flowable substance is drawn through the holes in the electrodes 128 and the micropores of the balloon 120, as needed, to lower the temperature of the region and prevent collateral thermal damage. Double lumen tubing permits constant circulation of the flowable substance throughout the bladder and balloon 120. The nature, temperature and amount of flowable substance are responsive to judgments by medical or veterinary personnel.

In a step 810, all or most of the flowable liquid that has been circulated through the electrodes 128 and balloon is siphoned of by the application of negative force to female coupling 134.

In a step 811, the balloon 120 is deflated by negative pressure on the syringe connected to female coupling 133.

In a step 812, the catheter 1 10 is withdrawn from the rectum.

Eighth Method of Operation

Figure 9:
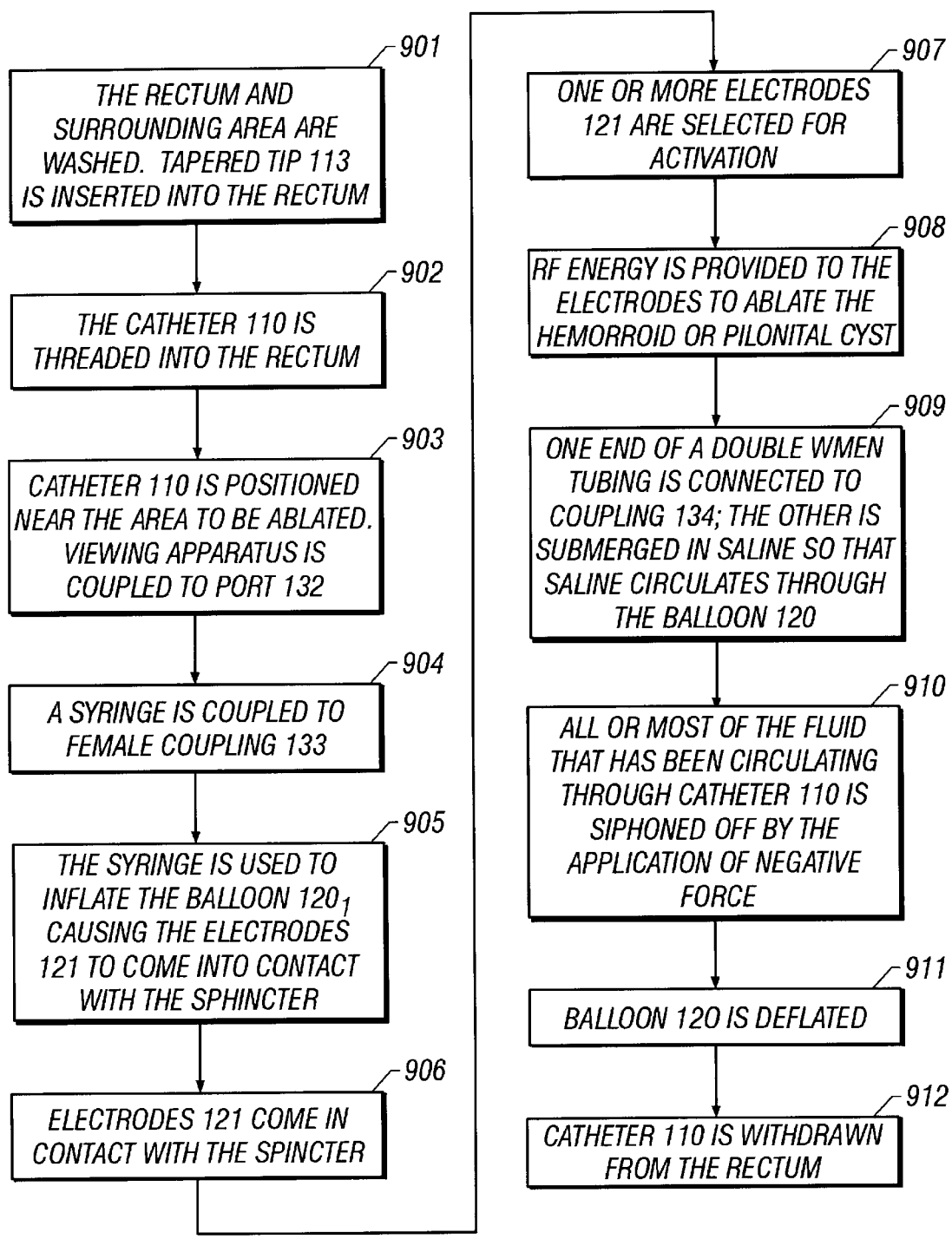
FIG. 9 is a process flow diagram for treatment of a hemorrhoid or pilonital cyst.

FIG. 9 is a process flow diagram of a method for treatment of a hemorrhoid.

A method 900 is performed using a catheter and electrode assembly 100.

In a step 901, the tapered tip 113 of the catheter 110 is well lubricated. The rectum and surrounding area are washed with a cleansing agent such as benzalonium chloride. Due to the potential for inducing pain, the area surrounding the rectum may be pretreated with a topical anesthetic before insertion; depending upon the circumstances, a muscle relaxant may be indicated.

The preferred size of the catheter 110 will be responsive to the orifice through which the catheter is inserted. The choice of pharmaceutical agents to be infused prior to or during treatment will be responsive to judgments by medical personnel, and may include lubricants, anesthetics, antispasmodics, anti-inflammatories, antibiotics or other agents.

In a step 902, the catheter 110 is introduced into the rectum and advanced along the walls of the sphincter. Since hemorrhoids and pilonital cysts may occur anywhere along this passage, the distance that the catheter is introduced is responsive to the judgment of medical or veterinary personnel.

In a step 903, the catheter 110 is positioned near the internal hemorrhoid, external hemorrhoid or cyst that is targeted for ablation. In the preferred embodiment, viewing apparatus coupled to the port 132 may be used to examine the region and determine which specific tissues are targeted for ablation.

In a step 904, a syringe is connected to the female coupling 133.

In a step 905, the syringe is used to exert positive pressure and inflate the inflatable, microporous balloon 120 with air or liquid. Inflation of the balloon 120 serves several purposes. In addition to positioning the electrodes 121, 128, the balloon 120 also helps anchor the catheter 110, seal off the region and prevent contamination with fecal matter. In an alternative embodiment, a second balloon is used to help seal off the area from contaminants.

In a step 906, inflation of the balloon 120 causes the set of electrodes 121, 128 to be brought into contact with the interior wall of the sphincter. Any corrections in the positioning of the catheter 110 are made at this time, using the anoscope coupled to port 132.

In a step 907, one or more electrodes 121, 128 are selected for activation. The number and pattern of selected electrodes is responsive to the judgment of medical or veterinary personnel. The mechanical switch 136 is used to select the electrodes 121, 128.

In a step 908, a source of RF energy is applied to port 131. RF energy is provided to electrodes 121, 128 so as to ablate the targeted portions of the rectum and anus. In a preferred embodiment, the RF energy has a frequency between 435 kilohertz and 485 kilohertz. The tissue immediately near the electrodes receives the RF energy. The tissue is heated for a short period of time until ablation occurs. In an alternative embodiment, the electrodes are controlled by a feedback technique using at least one sensor 126 such as an impedance or temperature sensor.

In a step 909, one end of a piece of biologically nonreactive double-lumen tubing is attached to female coupling 134; the other end of the tubing is attached to a pump which is submerged in a bath of saline or other flowable substance that is maintained at a constant temperature. The saline or flowable substance is drawn through the holes in the electrodes 128 and the micropores of the balloon 120, as needed, to lower the temperature of the region and prevent collateral thermal damage. Double lumen tubing permits constant circulation of the flowable substance throughout the bladder and balloon 120. The nature, temperature and amount of flowable substance are responsive to judgments by medical or veterinary personnel.

In a step 910, all or most of the flowable liquid that has been circulating through the electrodes 128 and balloon is siphoned of by the application of negative force to female coupling 134.

In a step 911, the balloon 120 is deflated by negative pressure on the syringe connected to female coupling 133.

Steps 905 through 911 are repeated as necessary until all hemorrhoids or cysts are removed.

In a step 912, the catheter 110 is withdrawn from the rectum.

Ninth Method of Operation

Figure 10:
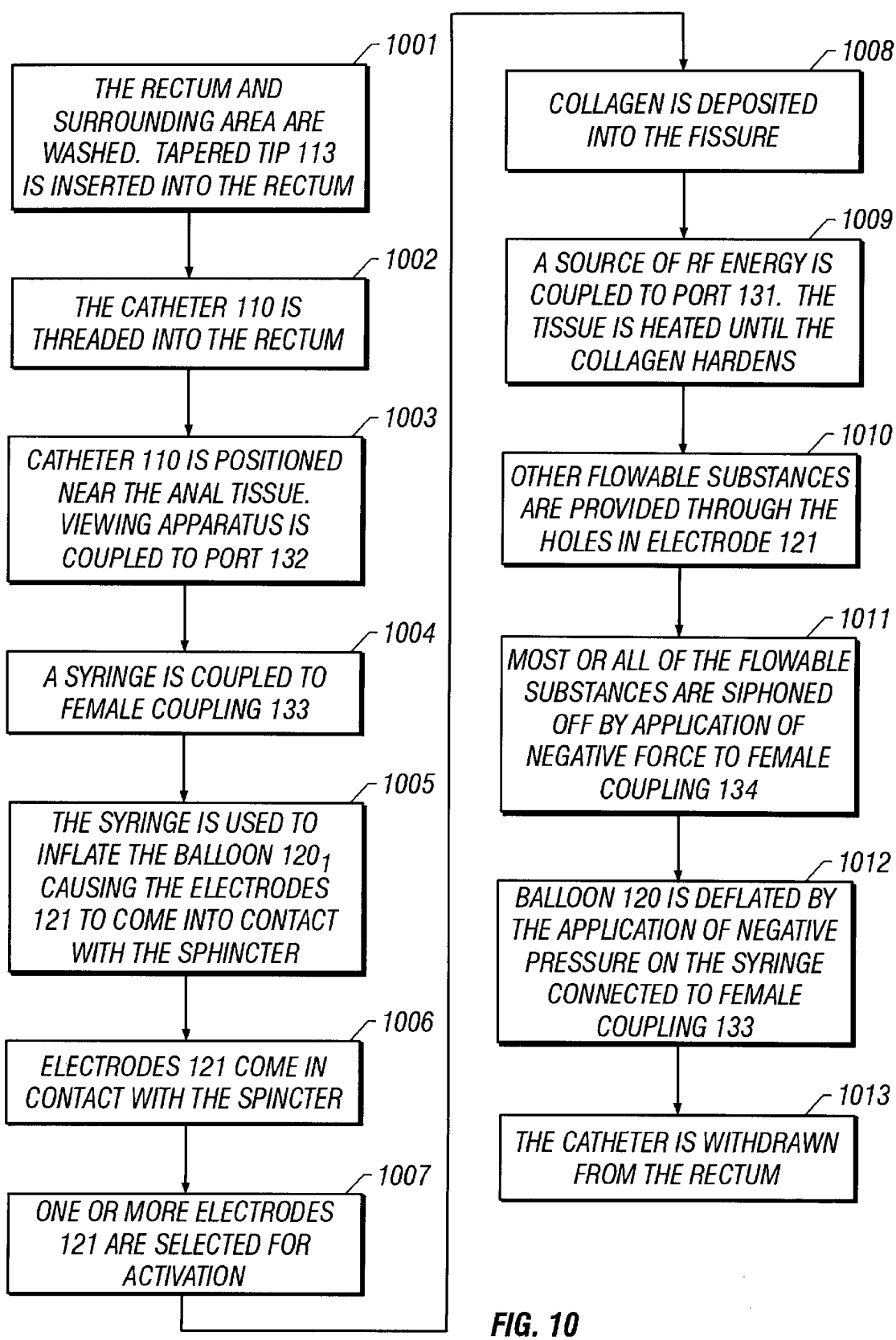
FIG. 10 is a process flow diagram for treatment of an anal fissure.

FIG. 10 is a process flow diagram of a method for treatment of an anal fissure.

A method 1000 is performed using a catheter and electrode assembly 100.

In a step 1001, the tapered tip 113 of the catheter 110 is well lubricated. The rectum and surrounding area are washed with a cleansing agent such as benzalonium chloride. Due to the potential for inducing pain, the area surrounding the rectum may be pretreated with a topical anesthetic before insertion; depending upon the circumstances, a muscle relaxant may be indicated.

The preferred size of the catheter 110 will be responsive to the orifice through which the catheter is inserted. The choice of pharmaceutical agents to be infused prior to or during treatment will be responsive to judgments by medical or veterinary personnel, and may include lubricants, anesthetics, antispasmodics, antiinflammatories, antibiotics or other agents.

In a step 1002, the catheter 110 is introduced into the rectum and advanced along the walls of the sphincter. The distance that the catheter is introduced is responsive to the judgment of medical or veterinary personnel.

In a step 1003, the catheter 110 is positioned near an anal fissure. In the preferred embodiment, viewing apparatus coupled to the port 132 may be used to examine the region and determine which specific tissues are targeted for ablation and where collagen should be deposited.

In a step 1004, a syringe is connected to the female coupling 133.

In a step 1005, the syringe is used to exert positive pressure and inflate the balloon 120 with air or with a liquid. Inflation of the balloon 120 serves several purposes. In addition to positioning the electrodes 121, 128, the balloon 120 also helps anchor the catheter. In an alternative embodiment, a second balloon 1201 is used to seal off the area from contaminants.

In a step 1007, inflation of the balloon 120 causes the set of electrodes to be brought into contact with the sphincter.

In a step 1008, one or more electrodes 121, 128 are selected for activation. The number and pattern of selected electrodes is responsive to the judgment of medical and veterinary personnel. The mechanical switch 136 is used to select the electrodes 121, 128 for activation.

In a step 1009, collagen is deposited into the fissure.

In a step 1010, a source of RF energy is coupled to port 131. RF energy is provided to the electrodes 121, 128 so as to harden the collagen for filling the fissure. In a preferred embodiment, the RF energy has a frequency between 435 kilohertz and 485 kilohertz. The RF energy is received by the tissue immediately near the electrodes. The tissue is heated for a short period of time until the collagen is sufficiently hardened. In an alternative embodiment, the electrodes are controlled by a feedback technique using at least one sensor 126 such as an impedance or temperature sensor.

In a step 1011, other flowable substances are provided through the holes in the electrodes 121, 128, if needed to immediately cool down the region and prevent collateral thermal damage. The nature, temperature and amount of the flowable substance are responsive to judgments by medical or veterinary personnel.

In a step 1012, most or all of the saline and other flowable substances are siphoned off by application of negative force to the female coupling 134.

In a step 1013, the balloon 120 is deflated by negative pressure on the syringe connected to female coupling 133.

In a step 1014, the catheter 110 is withdrawn from the rectum.

Tenth Method of Operation

Figure 11A:
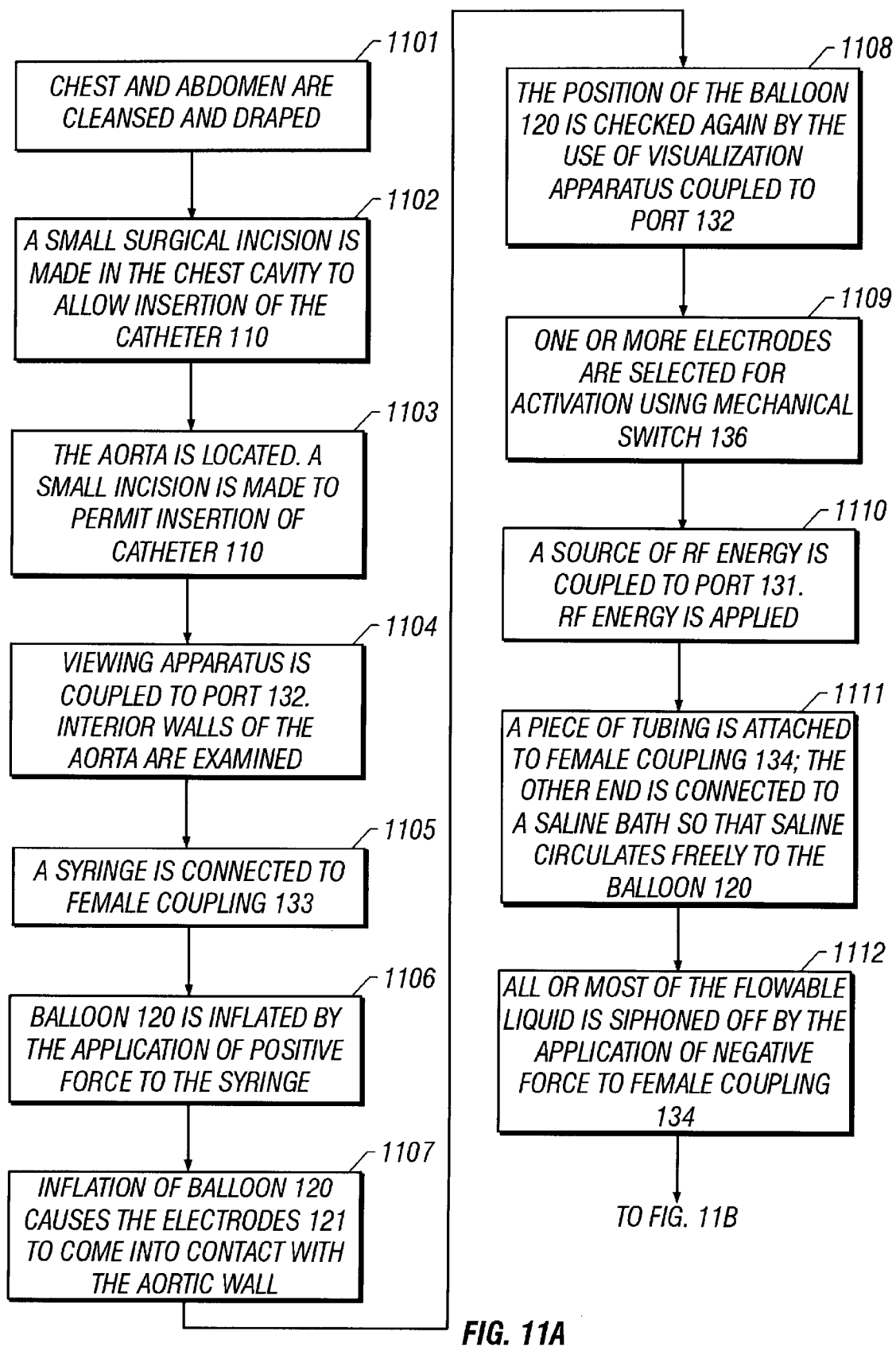
FIGS. 11A and 11B is a process flow diagram for treatment of an aortic aneurysm.
Figure 11B:
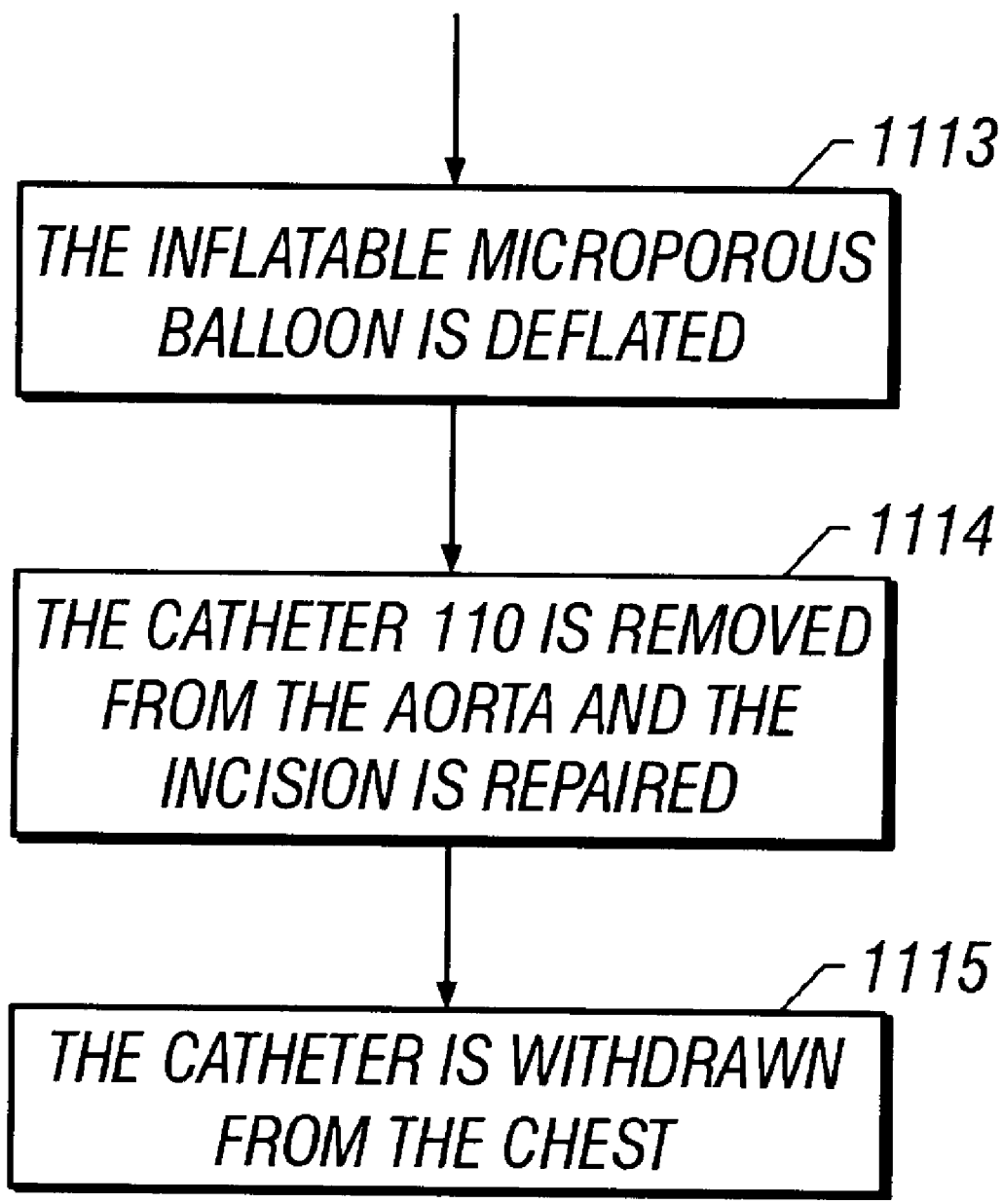

FIG. 11 is a process flow diagram of a method for treating of an aortic aneurysm.

An aortic aneurysm involves destruction of all three layers of the aortic wall. Thinning of the wall increases the diameter of the aorta, which in turn affects the pressure on the wall. Unless treated, the likelihood of rupture increases. Although often successful, surgical treatment for aortic aneurysm is frequently avoided because it's associated high morbidity. Research has shown that application of RF energy to the wall of the aorta increases the density of the wall. This increase in density has the reverse effect: the diameter of the aortic decreases, which in turn decreases the pressure on the aortic wall. The goals of this method of treatment include the increasing the density of the aortic wall.

A method 1100 is performed using a catheter and electrode assembly 100.

In a step 1101, the chest and/or abdominal region are cleansed and draped.

In a step 1102, a small surgical incision is made in the chest cavity to allow the insertion of the catheter 110. Strict aseptic technique is maintained during this step and all subsequent ones. Due to the potential for inducing pain, the surface of the skin may be pretreated with a topical anesthetic before insertion. A mild anesthetizing agent such as VerSed may be indicated. The choice of pharmaceutical agents to be infused prior to or during treatment will be responsive to judgments by medical personnel and may include lubricants, anesthetics, antispasmodics, antiinflammatories, antibiotics or other agents.

In a step 1103, the aorta is located. A second small incision is made into the wall of the aorta to permit insertion of the catheter 110. Care is taken not to abrade or damage adjacent structures.

In a step 1104, viewing apparatus is coupled to port 132. This viewing apparatus is used to examine the interior walls of the aorta, search for aneurysms (including dissecting aneurysms), evaluate the position of the catheter 110 and balloon 120, and determine which areas are targeted for application of RF energy.

In a step 1105, a syringe is connected to the female coupling 133 included in the control and delivery 130.

In a step 1106, the syringe is used to exert positive pressure and inflate the balloon 120 with air or with a liquid. Inflation of the balloon 120 serves several purposes. Inflation of the balloon 120 causes the electrodes 121, 128 to be positioned snugly against the aortic walls. Moreover, the inflatable, microporous balloon 120 also helps anchor the catheter in place.

In a step 1107, inflation of the balloon 120 causes the set of electrodes to be brought into contact with the damaged aortic wall.

In a step 1108, the position of the catheter and the balloon is checked once again using the visual apparatus coupled through port 132. Any correction to the position of the catheter 110 is made at this time, by repeating steps 503 through 1103 through 1107.

In a step 1109, one or more electrodes 121, 128 are selected for activation. The number and pattern of selected electrodes is responsive to the judgment of medical and veterinary personnel. The mechanical switch 136 is used to select the electrodes 121, 128 for activation.

In a step 1110, a source of RF energy is coupled to port 131. RF energy is provided to the electrodes 121, 128 so as to harden the collagen for filling the fissure. In a preferred embodiment, the RF energy has a frequency between 435 kilohertz and 485 kilohertz. The RF energy is received by the tissue immediately near the electrodes for a period of time less than ten minutes. The duration of time and frequency of energy are responsive to judgments of medical personnel.

In a step 1111, one end of a piece of biologically nonreactive double-lumen tubing is attached to female coupling 134; the other end of the tubing is attached to a pump which is submerged in a bath of saline or other flowable substance that is maintained at a constant temperature. The saline or flowable substance is drawn through the holes in the electrodes 128 and the micropores of the balloon 120, as needed, to lower the temperature of the region and prevent collateral thermal damage. Double lumen tubing permits constant circulation of the flowable substance throughout the bladder and balloon 120. The nature, temperature and amount of flowable substance are responsive to judgments by medical or veterinary personnel.

In a step 1112, all or most of the flowable liquid that has been circulating through the electrodes 128 and micropores of the balloon is siphoned off by the application of negative force to female coupling 134.

In a step 1113, the inflatable, microporous balloon 120 is deflated by application of negative pressure on the syringe connected to female coupling 133.

In a step 1114, the catheter 110 is removed from the aorta and the incision in the aorta is repaired.

In a step 1115, the catheter 110 is withdrawn from the incision where it was initially introduced into the body.

In a step 1116, the initial incision in the wall of the chest or abdomen is repaired.

Alternative Embodiments

Although preferred embodiments are disclosed herein, many variations are possible which remain within the concept, scope and spirit of the invention, and these variations would become clear to those skilled in the art after perusal of this application.

What is claimed is:

1. Apparatus comprising:
   a catheter disposed for insertion into a body at a selected location;
   a microporous, inflatable balloon coupled to said catheter, said inflatable balloon having at least one surface, said balloon being capable of allowing passage of a flowable substance through said one surface;
   one or more electrodes coupled proximately to said one surface, said electrode capable of delivering electromagnetic energy; and
   at least one of an electromagnetic impedance sensor, an optical sensor, and a temperature sensor housed in each electrode, for providing feedback to said electrodes.

2. Apparatus as in claim 1, said electrodes adapted for independent control of each other, wherein said electrodes are activated in any of numbers, patterns, and sequences selectable by means of a mechanical switch.

3. Apparatus as in claim 2, said electrodes arranged in one or more arrays, said selectable numbers, patterns or sequences including said arrays.

4. Apparatus as in claim 1, wherein said catheter is disposed for either laporoscopic or manual insertion into said selected location.

5. Apparatus as in claim 1, wherein said electromagnetic energy includes RF energy at about 400 to about 500 kilohertz.

6. Apparatus as in claim 1, including a blocking element coupled to said catheter, said blocking element comprising an inflatable balloon, said inflatable balloon being disposed to present a liquid-tight seal in a region proximate to said selected location.

7. Apparatus as in claim 1, including a coupling element adapted for delivery of a cooling fluid to said selected location.

8. Apparatus as in claim 1, including at least one lumen for delivering a flowable substance to said selected location, said flowable substance being responsive to said electromagnetic energy.

9. Apparatus as in claim 8, wherein said flowable substance has a selected response to said electromagnetic energy, said selected response including receiving said electromagnetic energy for ablation, coating, expansion, plumping, shaping, or shrinking tissue.

10. Apparatus as in claim 1, including a port adapted to couple with a source of energy.

11. Apparatus as in claim 10, wherein a controlled application includes uniform distribution of said electromagnetic energy in said interior region.

12. Apparatus as in claim 1, wherein said catheter includes at least one lumen capable of delivery of a flowable substance from outside the body to said elected location.

13. Apparatus as in claim 12, wherein said flowable substance includes at least one of: a drug, a gas, a radioisotope, an analgesic, an antibiotic, an anti-inflammatory, an anti-spasmodic, or saline.

14. Apparatus as in claim 1, wherein
    said selected location is disposed within a human being or other mammal; and
    said electromagnetic energy is delivered proximate to said selected location to a sphincter, to muscle tissue, or to nerve tissue.

15. Apparatus as in claim 14, wherein said sphincter or tissue is proximate to a bladder, esophagus, uterus, fallopian tube or vas deferens, sinus cavity, aorta, larynx, or pharynx.

* * * * *